US012644120B2

(12) United States Patent
Yang et al.

(10) Patent No.: US 12,644,120 B2
(45) Date of Patent: Jun. 2, 2026

(54) NUCLEIC ACID MOLECULE TARGETING MUTATION SITE OF CYP4V2 GENE AND USE THEREOF

(71) Applicant: CHIGENOVO CO., LTD., Beijing (CN)

(72) Inventors: Liping Yang, Beijing (CN); Xiang Meng, Beijing (CN); Shaohong Chen, Beijing (CN)

(73) Assignee: CHIGENOVO CO., LTD., Beijing (CN)

( * ) Notice: Subject to any disclaimer, the term of this patent is extended or adjusted under 35 U.S.C. 154(b) by 558 days.

(21) Appl. No.: 18/246,429

(22) PCT Filed: Sep. 24, 2020

(86) PCT No.: PCT/CN2020/117499
§ 371 (c)(1),
(2) Date: Mar. 23, 2023

(87) PCT Pub. No.: WO2022/061663
PCT Pub. Date: Mar. 31, 2022

(65) Prior Publication Data
US 2024/0263176 A1 Aug. 8, 2024

(51) Int. Cl.
| *C12N 15/113* | (2010.01) |
| *A61K 9/00* | (2006.01) |
| *A61K 31/7088* | (2006.01) |
| *A61K 48/00* | (2006.01) |
| *A61P 27/02* | (2006.01) |
| *C12N 15/86* | (2006.01) |

(52) U.S. Cl.
CPC .......... *C12N 15/113* (2013.01); *A61K 9/0019* (2013.01); *A61K 31/7088* (2013.01); *A61K 48/005* (2013.01); *A61K 48/0075* (2013.01); *A61P 27/02* (2018.01); *C12N 15/86* (2013.01); *C12N 2750/14143* (2013.01)

(58) Field of Classification Search
CPC .................. C12N 15/113; C12N 15/86; C12N 2750/14143; C12N 15/1137; C12N 15/52; C12N 2310/20; A61K 9/0019; A61K 48/005
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

2020/0255859 A1* 8/2020 Yang .................. A61K 38/1709

FOREIGN PATENT DOCUMENTS

| CN | 103468820 A | 12/2013 |
| CN | 111500635 A | 8/2020 |
| CN | 111630170 A | 9/2020 |
| WO | WO 2019025984 A1 | 2/2019 |

OTHER PUBLICATIONS

Extended European Search Report issued in application No. 20954515.1, dated May 7, 2024.
Xiaohui Zhang et al. "CYP4V2 mutation screening in an Iranian Bietti crystalline dystrophy 1-20, 25 pedigree and evidence for clustering of CYP4V2 mutations" Journal of Current Ophthalmology, vol. 31, No. 2, Mar. 2, 2019 (Mar. 2, 2019), pp. 172-179.
International Search Report and Written Opinion issued in application No. PCT/CN2020/117499, dated Jun. 29, 2021.

* cited by examiner

*Primary Examiner* — Jane J Zara
(74) *Attorney, Agent, or Firm* — KNOBBE, MARTENS, OLSON & BEAR, LLP

(57) ABSTRACT

The present application relates to a gRNA targeting CYP4V2 gene, and a donor nucleic acid molecule comprising a CYP4V2 gene fragment. The present application also relates to use of the gRNA and the donor nucleic acid molecule in the preparation of a medicament for treating Bietti crystalline dystrophy.

18 Claims, 12 Drawing Sheets

Specification includes a Sequence Listing.

EF1-α
promoter   FLAG   CYP4V2-repeated bases        P2A      EGFP                    SV40 PolyA

SEQUENCE LISTING

```
<160> NUMBER OF SEQ ID NOS: 54

<210> SEQ ID NO 1
<211> LENGTH: 21
<212> TYPE: DNA
<213> ORGANISM: Artificial Sequence
<220> FEATURE:
<223> OTHER INFORMATION: sgRNA1

<400> SEQUENCE: 1
ctgggctcta ggaattccac c                                        21

<210> SEQ ID NO 2
<211> LENGTH: 21
<212> TYPE: DNA
<213> ORGANISM: Artificial Sequence
<220> FEATURE:
<223> OTHER INFORMATION: sgRNA2

<400> SEQUENCE: 2
cataggctcc atagtcctac a                                        21

<210> SEQ ID NO 3
<211> LENGTH: 21
<212> TYPE: DNA
<213> ORGANISM: Artificial Sequence
<220> FEATURE:
<223> OTHER INFORMATION: sgRNA3

<400> SEQUENCE: 3
cagaaatcgc aagcatagag g                                        21

<210> SEQ ID NO 4
<211> LENGTH: 21
<212> TYPE: DNA
<213> ORGANISM: Artificial Sequence
<220> FEATURE:
<223> OTHER INFORMATION: sgRNA4

<400> SEQUENCE: 4
gcagtctttc caacacaaga a                                        21

<210> SEQ ID NO 5
<211> LENGTH: 21
<212> TYPE: DNA
<213> ORGANISM: Artificial Sequence
<220> FEATURE:
<223> OTHER INFORMATION: sgRNA5

<400> SEQUENCE: 5
```

-continued agtgtgatca cctggttata g                                                              21

<210> SEQ ID NO 6
<211> LENGTH: 21
<212> TYPE: DNA
<213> ORGANISM: Artificial Sequence
<220> FEATURE:
<223> OTHER INFORMATION: sgRNA6

<400> SEQUENCE: 6
aaaagttctg gaaatgaacg g                                                              21

<210> SEQ ID NO 7
<211> LENGTH: 21
<212> TYPE: DNA
<213> ORGANISM: Artificial Sequence
<220> FEATURE:
<223> OTHER INFORMATION: sgRNA7

<400> SEQUENCE: 7
tgtatatggt ccgtacctga a                                                              21

<210> SEQ ID NO 8
<211> LENGTH: 6
<212> TYPE: DNA
<213> ORGANISM: Artificial Sequence
<220> FEATURE:
<223> OTHER INFORMATION: sgRNA1-PAM

<400> SEQUENCE: 8 aagaat                                                                               6

<210> SEQ ID NO 9
<211> LENGTH: 6
<212> TYPE: DNA
<213> ORGANISM: Artificial Sequence
<220> FEATURE:
<223> OTHER INFORMATION: sgRNA2-PAM

<400> SEQUENCE: 9 ccgggt                                                                               6

<210> SEQ ID NO 10
<211> LENGTH: 6
<212> TYPE: DNA
<213> ORGANISM: Artificial Sequence
<220> FEATURE:
<223> OTHER INFORMATION: sgRNA3-PAM

<400> SEQUENCE: 10 gtgaat                                                                               6

<210> SEQ ID NO 11
<211> LENGTH: 6
<212> TYPE: DNA
<213> ORGANISM: Artificial Sequence
<220> FEATURE:
<223> OTHER INFORMATION: sgRNA4-PAM

<400> SEQUENCE: 11 tagaat                                                                               6

<210> SEQ ID NO 12
<211> LENGTH: 6
<212> TYPE: DNA
<213> ORGANISM: Artificial Sequence -continued

```
<220> FEATURE:
<223> OTHER INFORMATION: sgRNA5-PAM

<400> SEQUENCE: 12 gagaat                                                               6

<210> SEQ ID NO 13
<211> LENGTH: 5
<212> TYPE: DNA
<213> ORGANISM: Artificial Sequence
<220> FEATURE:
<223> OTHER INFORMATION: sgRNA6-PAM

<400> SEQUENCE: 13 tgggg                                                                5

<210> SEQ ID NO 14
<211> LENGTH: 5
<212> TYPE: DNA
<213> ORGANISM: Artificial Sequence
<220> FEATURE:
<223> OTHER INFORMATION: sgRNA7-PAM

<400> SEQUENCE: 14 aggaa                                                                5

<210> SEQ ID NO 15
<211> LENGTH: 26
<212> TYPE: DNA
<213> ORGANISM: Artificial Sequence
<220> FEATURE:
<223> OTHER INFORMATION: CYP4V2sgRNA1-F

<400> SEQUENCE: 15
caccgctggg ctctaggaat tccacc                                         26

<210> SEQ ID NO 16
<211> LENGTH: 26
<212> TYPE: DNA
<213> ORGANISM: Artificial Sequence
<220> FEATURE:
<223> OTHER INFORMATION: CYP4V2sgRNA1-R

<400> SEQUENCE: 16
aaacggtgga attcctagag cccagc                                         26

<210> SEQ ID NO 17
<211> LENGTH: 26
<212> TYPE: DNA
<213> ORGANISM: Artificial Sequence
<220> FEATURE:
<223> OTHER INFORMATION: CYP4V2sgRNA2-F

<400> SEQUENCE: 17
caccgcatag gctccatagt cctaca                                         26

<210> SEQ ID NO 18
<211> LENGTH: 26
<212> TYPE: DNA
<213> ORGANISM: Artificial Sequence
<220> FEATURE:
<223> OTHER INFORMATION: CYP4V2sgRNA2-R

<400> SEQUENCE: 18
aaactgtagg actatggagc ctatgc                                         26
```

-continued

```
<210> SEQ ID NO 19
<211> LENGTH: 26
<212> TYPE: DNA
<213> ORGANISM: Artificial Sequence
<220> FEATURE:
<223> OTHER INFORMATION: CYP4V2sgRNA3-F

<400> SEQUENCE: 19
caccgcagaa atcgcaagca tagagg                                    26

<210> SEQ ID NO 20
<211> LENGTH: 26
<212> TYPE: DNA
<213> ORGANISM: Artificial Sequence
<220> FEATURE:
<223> OTHER INFORMATION: CYP4V2sgRNA3-R

<400> SEQUENCE: 20
aaaccctcta tgcttgcgat ttctgc                                    26

<210> SEQ ID NO 21
<211> LENGTH: 26
<212> TYPE: DNA
<213> ORGANISM: Artificial Sequence
<220> FEATURE:
<223> OTHER INFORMATION: CYP4V2sgRNA4-F

<400> SEQUENCE: 21
caccggcagt ctttccaaca caagaa                                    26

<210> SEQ ID NO 22
<211> LENGTH: 26
<212> TYPE: DNA
<213> ORGANISM: Artificial Sequence
<220> FEATURE:
<223> OTHER INFORMATION: CYP4V2sgRNA4-R

<400> SEQUENCE: 22
aaacttcttg tgttggaaag actgcc                                    26

<210> SEQ ID NO 23
<211> LENGTH: 26
<212> TYPE: DNA
<213> ORGANISM: Artificial Sequence
<220> FEATURE:
<223> OTHER INFORMATION: CYP4V2sgRNA5-F

<400> SEQUENCE: 23
caccgagtgt gatcacctgg ttatag                                    26

<210> SEQ ID NO 24
<211> LENGTH: 26
<212> TYPE: DNA
<213> ORGANISM: Artificial Sequence
<220> FEATURE:
<223> OTHER INFORMATION: CYP4V2sgRNA5-R

<400> SEQUENCE: 24
aaacctataa ccaggtgatc acactc                                    26

<210> SEQ ID NO 25
<211> LENGTH: 26
<212> TYPE: DNA
<213> ORGANISM: Artificial Sequence
<220> FEATURE:
<223> OTHER INFORMATION: CYP4V2sgRNA6-F
```

-continued

<400> SEQUENCE: 25
caccgaaaag ttctggaaat gaacgg                                                26

<210> SEQ ID NO 26
<211> LENGTH: 26
<212> TYPE: DNA
<213> ORGANISM: Artificial Sequence
<220> FEATURE:
<223> OTHER INFORMATION: CYP4V2sgRNA6-R

<400> SEQUENCE: 26
aaacccgttc atttccagaa cttttc                                                26

<210> SEQ ID NO 27
<211> LENGTH: 26
<212> TYPE: DNA
<213> ORGANISM: Artificial Sequence
<220> FEATURE:
<223> OTHER INFORMATION: CYP4V2sgRNA7-F

<400> SEQUENCE: 27
caccgtgtat atggtccgta cctgaa                                                26

<210> SEQ ID NO 28
<211> LENGTH: 26
<212> TYPE: DNA
<213> ORGANISM: Artificial Sequence
<220> FEATURE:
<223> OTHER INFORMATION: CYP4V2sgRNA7-R

<400> SEQUENCE: 28
aaacttcagg tacggaccat atacac                                                26

<210> SEQ ID NO 29
<211> LENGTH: 21
<212> TYPE: DNA
<213> ORGANISM: Artificial Sequence
<220> FEATURE:
<223> OTHER INFORMATION: CYP4V2sgRNA1-P1-F

<400> SEQUENCE: 29
tggagttatg tccttgtggt g                                                     21

<210> SEQ ID NO 30
<211> LENGTH: 21
<212> TYPE: DNA
<213> ORGANISM: Artificial Sequence
<220> FEATURE:
<223> OTHER INFORMATION: CYP4V2sgRNA1-P1-R

<400> SEQUENCE: 30
cctgctacta agtggcctga a                                                     21

<210> SEQ ID NO 31
<211> LENGTH: 20
<212> TYPE: DNA
<213> ORGANISM: Artificial Sequence
<220> FEATURE:
<223> OTHER INFORMATION: CYP4V2sgRNA2/6-P2.6-F

<400> SEQUENCE: 31
cgtcattccc acgattgcct                                                       20

<210> SEQ ID NO 32

-continued

```
<211> LENGTH: 21
<212> TYPE: DNA
<213> ORGANISM: Artificial Sequence
<220> FEATURE:
<223> OTHER INFORMATION: CYP4V2sgRNA2/6-P2.6-R

<400> SEQUENCE: 32
tggtggttag cacttagcga g                                            21

<210> SEQ ID NO 33
<211> LENGTH: 22
<212> TYPE: DNA
<213> ORGANISM: Artificial Sequence
<220> FEATURE:
<223> OTHER INFORMATION: CYP4V2sgRNA3/4-P3.4-F

<400> SEQUENCE: 33
aagcatggca gtgtttgagt tg                                           22

<210> SEQ ID NO 34
<211> LENGTH: 20
<212> TYPE: DNA
<213> ORGANISM: Artificial Sequence
<220> FEATURE:
<223> OTHER INFORMATION: CYP4V2sgRNA3/4-P3.4-R

<400> SEQUENCE: 34
cgttcatttc attggcccgt                                              20

<210> SEQ ID NO 35
<211> LENGTH: 21
<212> TYPE: DNA
<213> ORGANISM: Artificial Sequence
<220> FEATURE:
<223> OTHER INFORMATION: CYP4V2sgRNA5-P5-F

<400> SEQUENCE: 35
cggcagtcat tttcaaaggc a                                            21

<210> SEQ ID NO 36
<211> LENGTH: 21
<212> TYPE: DNA
<213> ORGANISM: Artificial Sequence
<220> FEATURE:
<223> OTHER INFORMATION: CYP4V2sgRNA5-P5-R

<400> SEQUENCE: 36
caggcctcag taggcaattc t                                            21

<210> SEQ ID NO 37
<211> LENGTH: 21
<212> TYPE: DNA
<213> ORGANISM: Artificial Sequence
<220> FEATURE:
<223> OTHER INFORMATION: CYP4V2sgRNA7-P7-F

<400> SEQUENCE: 37
accaacagtg taagtccctg a                                            21

<210> SEQ ID NO 38
<211> LENGTH: 20
<212> TYPE: DNA
<213> ORGANISM: Artificial Sequence
<220> FEATURE:
<223> OTHER INFORMATION: CYP4V2sgRNA7-P7-R

<400> SEQUENCE: 38
```
acacagcacc ctgtttgttc                                                  20

<210> SEQ ID NO 39
<211> LENGTH: 774
<212> TYPE: DNA
<213> ORGANISM: Artificial Sequence
<220> FEATURE:
<223> OTHER INFORMATION: Donor

<400> SEQUENCE: 39
gtcatcgctg aacgggccaa tgaaatgaac gccaatgaag actgtagagg tgatggcagg      60
ggctctgccc cctccaaaaa taaacgcagg gcctttcttg acttgctttt aagtgtgact     120
gatgacgaag ggaacaggct aagtcatgaa gatattcgag aagaagttga caccttcatg     180
tttgaggggc acgatacaac tgcagctgca ataaactggt ccttatacct gttgggttct     240
aacccagaag tccagaaaaa agtggatcat gaattggatg acgtgtttgg gaagtctgac     300
cgtcccgcta cagtagaaga cctgaagaaa cttcggtatc tggaatgtgt tattaaggag     360
acccttcgcc tttttccttc tgttcctttta tttgcccgta gtgttagtga agattgtgaa     420
gtggcaggtt acagagttct aaaaggcact gaagccgtca tcattcccta tgcattgcac     480
agagatccga gatacttccc caaccccgag gagttccagc ctgagcggtt cttccccgag     540
aatgcacaag ggcgccatcc atatgcctac gtgcccttct ctgctggccc caggaactgt     600
ataggtcaaa agtttgctgt gatggaagaa aagaccattc tttcgtgcat cctgaggcac     660
ttttggatag aatccaacca gaaaagagaa gagcttggtc tagaaggaca gttgattctt     720
cgtccaagta atggcatctg gatcaagttg aagaggagaa atgcagatga acgc           774

<210> SEQ ID NO 40
<211> LENGTH: 714
<212> TYPE: DNA
<213> ORGANISM: Artificial Sequence
<220> FEATURE:
<223> OTHER INFORMATION: EGFP

<400> SEQUENCE: 40
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg ccccaccctc     180
gtgaccaccc tgacctacgg cgtgcagtgc ttcagccgct accccgacca catgaagcag     240
cacgacttct tcaagtccgc tatgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacgcccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caag           714

<210> SEQ ID NO 41
<211> LENGTH: 2073
<212> TYPE: DNA
<213> ORGANISM: Artificial Sequence
<220> FEATURE:

<223> OTHER INFORMATION: Intron

<400> SEQUENCE: 41
gtaagtccct gactttttaca attgtggtaa aatagacata acataaaatt tccctttata      60
accattttaa ctgtacagtt tggtggtatt aagtgcattc acgatgttgt gcaaccatcc     120
ccaccgttca tttccagaac ttttggtaag tccatgatgt tgatgttttg ttaacatacc     180
cggtgtagga ctatggagcc tatgtctcag aaaataaaac ttgaataata atagaaaaca     240 attttttcata taaaaaatta tacttaagta taaaaatgta tacttcaatt atgtagtcaa     300
caaatattaa ttaagtactc gctaagtgct aaccaccata ccaaatgttg gaaatgtagt     360
aatgagtagg acatgtgtat atggtccgta cctgaaagga agttattcta gtaggagagg     420
tgatctatca acacataatt acaacatgtg atatgagctg tgaacactta tgaacaaaca     480
gggtgctgtg taaaagaata aaggaacaaa gatctatgta taggagtttt ctggaaaatg     540
tttggattcg gcagtcattt tcaaaggcag agggcattga tagcagtatc ttaacatgga     600
aaacattaaa actaactaga tattagtatt ctatttccaa ttcaaaaata accagaagat     660
agtgatgttg ttttgaatat aggatgtcaa tctttgtgtt aataatgtgt tttgaaaaag     720
caagacttaa ttgaaaatat acatcaaatt ataatttcag tgtattaaaa aactgcctgt     780
ttaaatatgt cctttctttg ctgtaaattt tggttaaaat ctattggagt tatgtccttg     840
tggtgaagta caccctaccc ccaagagagc aaatgatgaa taaatcagta gatgttccat     900
gaatgcaatg ttggctgagc tggccacagt ggagtgtgat cacctggtta taggagaata     960
gccagcaggt tatatttcat aattatattt ttccttaaat tttgtgcatt aatatttaat    1020
agcaataatt aaatgaattc cagactgaat agacaatttt attcattgaa taaacattga    1080
gaattgccta ctgaggcctg ggctctagga attccaccaa gaataaaaaa agacatggtg    1140
ttttgccctc aaattgctta gaatctattc aggccactta gtagcaggtt tggtcaatta    1200
cctggtagga aaagaaggtt gaaatgtaca accaaattaa gtgtattggc cttcattctt    1260
ttatccatcc aagaaatatc tagtgagtat ttgttaaatg ccaagcagtg ctctagaggt    1320
tggaaatgta tcaatgaaca aagacatgca caagcatggc agtgtttgag ttgtaagaga    1380
aagatgctaa ataataagta taacgtaagt ataatatcac attataataa taagtatgac    1440
agaagtatca cataatgtca ggtggcaagg gaaatggaga aaaagcattg ttaggaggcg    1500
tcgcagtgct agggacaggg gtagcaggga tgagggaggt ctctctgatc gtgtgacaat    1560
gagcagagat ctggaagaag ggaggggggca gccgtgcagg cctctgagga aagcatttca    1620
ggcagcagaa atcgcaagca tagagggtga attcactaat ctgcttgctg tttctttttct    1680 cctctacaac atgtaattaa gtctataatt agactgttgt ataatgattg cattcactct    1740
accacttaaa cttttttctca ttagcgcaat ccaatctcta gggtactatc tagtagacta    1800
tgattctatt cttgtgttgg aaagactgca aaaatagcac ttgaaaatta ggaatttgcg    1860
tgacattaaa tttgttttta aaagtttcac cagataatcc ccaaaatatt aatgaggctt    1920
tactgtattt tcacaagagc ctatgttgtc gaaatgttga aataggctta gaaaaataaa    1980
tgaaagaaac tagcatattt tataagaaaa tgtgttaact agggtgcatc caagtccaaa    2040
cagaagcatg tgattatcat tcaaatcata cag                                 2073

<210> SEQ ID NO 42
<211> LENGTH: 21
<212> TYPE: DNA
<213> ORGANISM: Artificial Sequence

<220> FEATURE:
<223> OTHER INFORMATION: P1.5-F

<400> SEQUENCE: 42
gtgaagtaca ccctacccccc a                                                21

<210> SEQ ID NO 43
<211> LENGTH: 22
<212> TYPE: DNA
<213> ORGANISM: Artificial Sequence
<220> FEATURE:
<223> OTHER INFORMATION: P1.5-R

<400> SEQUENCE: 43
ccaggtaatt gaccaaacct gc                                                22

<210> SEQ ID NO 44
<211> LENGTH: 22
<212> TYPE: DNA
<213> ORGANISM: Artificial Sequence
<220> FEATURE:
<223> OTHER INFORMATION: P2.6.7-F

<400> SEQUENCE: 44
ggatgggaac acaaaaagag cc                                                22

<210> SEQ ID NO 45
<211> LENGTH: 23
<212> TYPE: DNA
<213> ORGANISM: Artificial Sequence
<220> FEATURE:
<223> OTHER INFORMATION: P2.6.7-R

<400> SEQUENCE: 45
acacagcacc ctgtttgttc ata                                               23

<210> SEQ ID NO 46
<211> LENGTH: 20
<212> TYPE: DNA
<213> ORGANISM: Artificial Sequence
<220> FEATURE:
<223> OTHER INFORMATION: P3.4-F

<400> SEQUENCE: 46
tgcacaagca tggcagtgtt                                                   20

<210> SEQ ID NO 47
<211> LENGTH: 21
<212> TYPE: DNA
<213> ORGANISM: Artificial Sequence
<220> FEATURE:
<223> OTHER INFORMATION: P3.4-R

<400> SEQUENCE: 47
catttcattg gcccgttcag c                                                 21

<210> SEQ ID NO 48
<211> LENGTH: 21
<212> TYPE: RNA
<213> ORGANISM: Artificial Sequence
<220> FEATURE:
<223> OTHER INFORMATION: sgRNA1-RNA

<400> SEQUENCE: 48
cugggcucua ggaauuccac c                                                 21

-continued

```
<210> SEQ ID NO 49
<211> LENGTH: 21
<212> TYPE: RNA
<213> ORGANISM: Artificial Sequence
<220> FEATURE:
<223> OTHER INFORMATION: sgRNA2-RNA

<400> SEQUENCE: 49
cauaggcucc auaguccuac a                                            21

<210> SEQ ID NO 50
<211> LENGTH: 21
<212> TYPE: RNA
<213> ORGANISM: Artificial Sequence
<220> FEATURE:
<223> OTHER INFORMATION: sgRNA3-RNA

<400> SEQUENCE: 50
cagaaaucgc aagcauagag g                                            21

<210> SEQ ID NO 51
<211> LENGTH: 21
<212> TYPE: RNA
<213> ORGANISM: Artificial Sequence
<220> FEATURE:
<223> OTHER INFORMATION: sgRNA4-RNA

<400> SEQUENCE: 51
gcagucuuuc caacacaaga a                                            21

<210> SEQ ID NO 52
<211> LENGTH: 21
<212> TYPE: RNA
<213> ORGANISM: Artificial Sequence
<220> FEATURE:
<223> OTHER INFORMATION: sgRNA5-RNA

<400> SEQUENCE: 52
agugugauca ccugguuaua g                                            21

<210> SEQ ID NO 53
<211> LENGTH: 21
<212> TYPE: RNA
<213> ORGANISM: Artificial Sequence
<220> FEATURE:
<223> OTHER INFORMATION: sgRNA6-RNA

<400> SEQUENCE: 53
aaaaguucug gaaaugaacg g                                            21

<210> SEQ ID NO 54
<211> LENGTH: 21
<212> TYPE: RNA
<213> ORGANISM: Artificial Sequence
<220> FEATURE:
<223> OTHER INFORMATION: sgRNA7-RNA

<400> SEQUENCE: 54
uguauauggu ccguaccuga a                                            21
```

NUCLEIC ACID MOLECULE TARGETING MUTATION SITE OF CYP4V2 GENE AND USE THEREOF

CROSS-REFERENCE TO RELATED APPLICATIONS

This application is the U.S. National Phase under 35 U.S.C. § 371 of International Application PCT/CN2020/117499, filed Sep. 24, 2020, the disclosure of which is incorporated by reference herein in its entirety.

REFERENCE TO ELECTRONIC SEQUENCE LISTING

The present application is filed along with an Electronic Sequence Listing. The Electronic Sequence Listing is provided as a file entitled CSPT088.005APC_ Replacement_ SEQ_LIST.TXT which is approximately 14 KB in size, created on Oct. 4, 2023. The information in the Electronic Sequence Listing is incorporated herein by reference in its entirety.

TECHNICAL FIELD

The application relates to the field of biomedicine, and in particular to gRNAs and donor nucleic acid molecules for treating the diseases with CYP4V2 gene mutation.

BACKGROUND

Bietti crystalline dystrophy (BCD), also known as crystalline retinitis pigmentosa, Bietti Crystalline Corneoretinal Dystrophy, Bietti Crystalline Retinopathy, Bietti's Retinal Dystrophy (OMIM 210370), is a blinding, autosomal recessive retinal degenerative disease. The CYP4V2 gene is one of the BCD pathogenic genes discovered so far (Li et al., Am J Hum Genet. 74:817-826, 200). CYP4V2 (polypeptide 2, subfamily V, family 4, cytochrome P450, synonym: CYP4AH1) belongs to the cytochrome P450 superfamily and is one member of ferroheme-thiolate protein cytochrome P450 subfamily 4 (CYP4).

Currently, there are many methods for treating this disease, such as gene replacement therapy in which the CYP4V2 wild-type gene is transfected into the mutant cells using a viral transfection system or other transfection systems (such as AAV, lentivirus, retrovirus) such that the mutant cells can express the wild-type CYP4V2. This approach can only partially restore the function of mutant cells, and the efficacy is limited. The reason is that the mutant gene products still exist in the cells, and these mutant proteins will exhibit competitive inhibition with respect to normal gene products. Thus, a safer and more effective therapy is urgently needed to be discovered.

The information disclosed in the BACKGROUND is only intended to facilitate the understanding of the general background of the present application, and should not be considered as acknowledging or implying in any way that this information constitutes the prior art well-known to those skilled in the art.

SUMMARY

The present application provides a gRNA specifically targeting polypeptide 2, subfamily V, family 4, cytochrome P450 (CYP4V2), which specifically binds to the intron region between exon 6 and exon 7 of the CYP4V2 gene. The gRNA has a good cleaving effect on the intron region between exon 6 and exon 7 of CYP4V2, such that the original CYP4V2 gene products do not exist in the cells. The present application also provides a donor nucleic acid molecule, comprising a nucleotide sequence between intron 6 and exon 11 of the CYP4V2 gene. The donor nucleic acid molecule can repair exons 7-11 of CYP4V2 in the mutant cells after the endogenous CYP4V2 is cleaved by the gRNA, to produce the CYP4V2 protein with a normal function, thus exhibiting a good repair effect. The present application provides a vector comprising the gRNA and/or the donor nucleic acid molecule. It can enable CYP4V2-mutated cells to express the correct polypeptide 2, subfamily V, family 4, cytochrome P450, and has a good gene editing and repair efficiency.

In one aspect, the present application provides a gRNA specifically targeting polypeptide 2, subfamily V, family 4, cytochrome P450 (CYP4V2) gene, which specifically binds to the intron region between exon 6 and exon 7 of the CYP4V2 gene.

In certain embodiments, the gRNA specifically binds to a nucleotide sequence set forth in SEQ ID NO: 41.

In certain embodiments, the gRNA comprises a nucleotide sequence set forth in any of SEQ ID NOs: 48-51.

In certain embodiments, the gRNA comprises 5'-(X)n-SEQ ID NO: 48-51-skeleton sequence-3', wherein X is a base selected from any of A, U, C, and G, and n is any integer from 0 to 15.

In certain embodiments, the gRNA is a single-stranded guide RNA (sgRNA).

In another aspect, the present application provides one or more isolated nucleic acid molecule(s) encoding the gRNA specifically targeting CYP4V2 gene.

In another aspect, the present application provides a donor nucleic acid molecule comprising a nucleotide sequence between intron 6 and exon 11 of CYP4V2 gene.

In certain embodiments, the donor nucleic acid molecule comprises a nucleotide sequence set forth in SEQ ID NO: 39.

In another aspect, the present application provides a vector comprising the isolated nucleic acid molecule and/or the donor nucleic acid molecule.

In certain embodiments, the vector, the isolated nucleic acid molecule, and the donor nucleic acid molecule are in a same vector.

In certain embodiments, the vector is a viral vector.

In another aspect, the present application provides a cell comprising the isolated nucleic acid molecule, the donor nucleic acid molecule, and/or the vector.

In certain embodiments, the cell comprises HEK293 cells, renal epithelial cells, and/or induced pluripotent stem cells.

In certain embodiments, the cell is modified to have a differentiation potential.

In certain embodiments, the cell can be differentiated into a 3D-retinal organoid.

In another aspect, the present application provides a pharmaceutical composition comprising the gRNA, the one or more isolated nucleic acid molecule(s), or the donor nucleic acid molecule, the vector, and a pharmaceutically acceptable carrier.

In another aspect, the present application provides a kit comprising the gRNA, the one or more isolated nucleic acid molecule(s), the donor nucleic acid molecule, or the vector.

In another aspect, the present application provides use of the gRNA, the one or more isolated nucleic acid molecule(s), the donor nucleic acid molecule, and/or the vector in the manufacture of a medicament for treating a disease, wherein the disease comprises a disease caused by a mutation in the CYP4V2 gene.

In certain embodiments, the mutation is located behind the intron between exon 6 and exon 7 of the CYP4V2 gene.

In certain embodiments, the disease comprises Bietti crystalline dystrophy.

In another aspect, the present application provides a method for treating the Bietti crystalline dystrophy, comprising the following steps: introducing the gRNA, the one or more isolated nucleic acid molecule(s), the donor nucleic acid molecule, and/or the vector into a subject in need thereof.

In certain embodiments, the CYP4V2 protein with a normal function is obtained upon the introducing.

In certain embodiments, the introducing comprises an injection.

In certain embodiments, the introducing comprises an injection in the subretinal space.

In another aspect, the present application provides a method for regulating the expression of CYP4V2 gene in cells, comprising introducing the gRNA, the one or more isolated nucleic acid molecule(s), and/or the vector into the cells.

Other aspects and advantages of the present application can be readily appreciated by those skilled in the art from the detailed descriptions below. Only exemplary embodiments of the present application are shown and described in the detailed descriptions below. As recognized by those skilled in the art, the disclosure of the present application will enable those skilled in the art to make changes to the particular embodiments without departing from the spirit and scope of the invention disclosed in the present application. Accordingly, the accompanying drawings and the descriptions in the specification of the present application are only exemplary and not limitative.

DESCRIPTION OF THE DRAWINGS

The particular features of the invention disclosed in the present application are set forth in the appended claims. The characteristics and advantages of the invention disclosed in the present application could be better understood by reference to the exemplary embodiments described in detail below and the accompanying drawings. Brief descriptions of the accompanying drawings are as follows:

DESCRIPTION OF EMBODIMENTS

Figure 1:
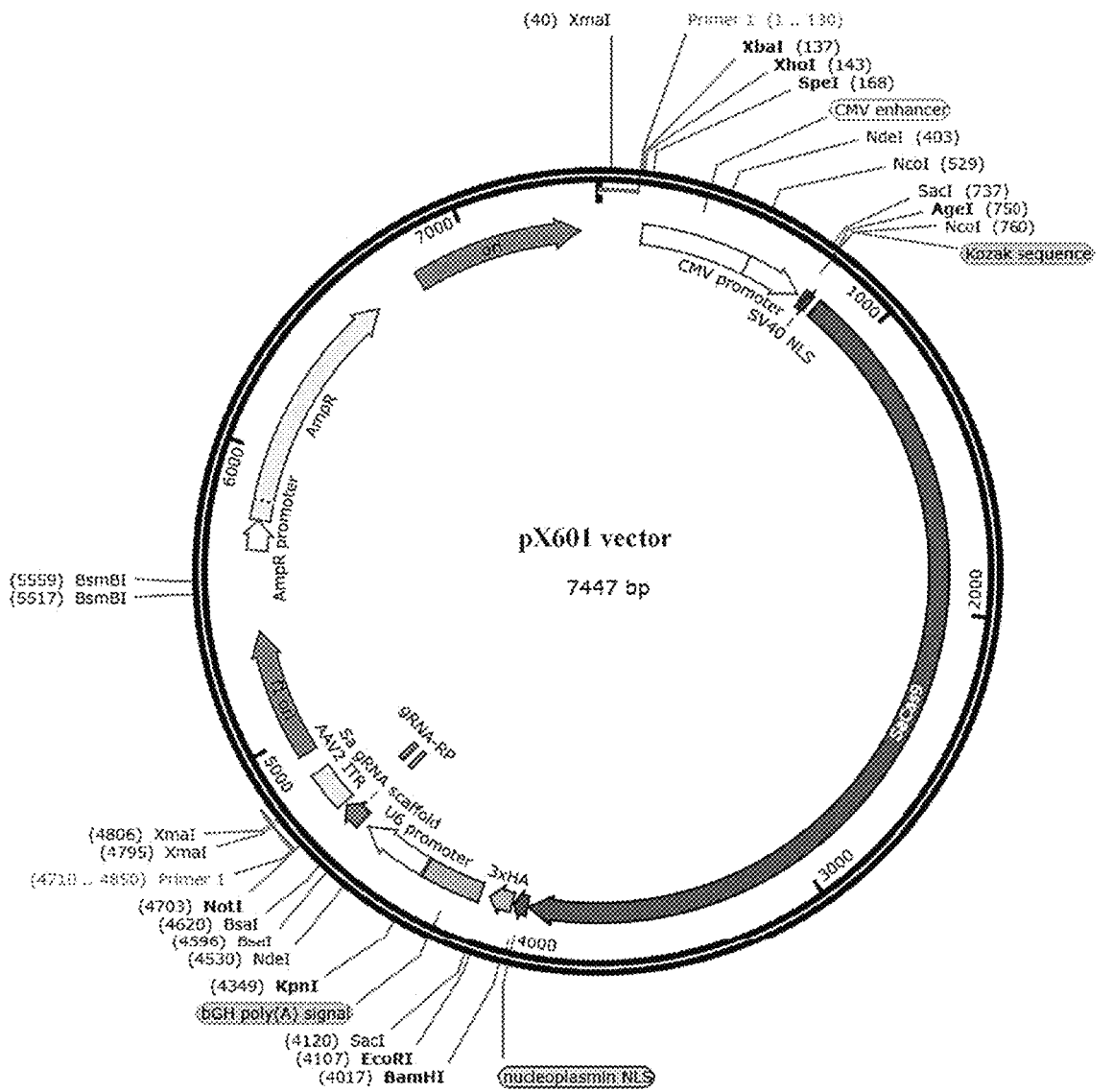
FIG. 1 shows the plasmid map of PX601 described in the present application.

The embodiments of the invention in the present application are described below by certain specific examples, and those skilled in the art could easily understand other advantages and effects of the invention in the present application from the disclosure of this specification.

Definitions of Terms

As used herein, the term "3D-retinal organoid" generally refers to an artificially grown retina having a three-dimensional structure, capable of self-renewal and self-organization, and exhibiting basic retinal functions (e.g., light perception). The 3D-retinal organoid can be differentiated from primary tissues or stem cells (e.g., pluripotent stem cells), with all the cells in the retina required for receiving lights and sending signals to the brain.

As used herein, the term "isolated nucleic acid molecule" is one which is separated from other nucleic acid molecules present in the natural source of said nucleic acid. Such an isolated nucleic acid molecule is removed or separated from its usual or natural environment, or the molecule is produced in such a way that it is not present in its usual or natural environment. It is isolated from polypeptides, peptides, lipids, carbohydrates, other polynucleotides, or other materials in the usual or natural environment. The isolated nucleic acid molecule described herein may encode RNA, for example, may encode a gRNA specifically targeting CYP4V2 gene.

As used herein, the term "donor nucleic acid molecule" generally refers to a nucleic acid molecule that provides a heterologous nucleic acid sequence to a recipient (e.g., receiving the nucleic acid molecule).

As used herein, the term "Bietti crystalline dystrophy" generally refers to a class of autosomal recessive ocular diseases. The symptoms mainly include crystals (transparent coverings) in the cornea; small, yellow or white, crystalline deposits deposited in the photosensitive tissues of the retina; and progressive atrophy of the retina, choriocapillary, and choroid. The Bietti crystalline dystrophy may include a disease caused by CYP4V2 gene mutation.

As used herein, the term "kit" generally refers to two or more components packaged together in a container, receptacle or other containers, one of which corresponds to the gRNA, the one or more isolated nucleic acid molecule(s), the donor nucleic acid molecule, and/or the vector, pharmaceutical composition or cell described herein. Thus, the kit may be described as a set of products and/or instruments sufficient to achieve a particular purpose, which may be sold as a single unit.

As used herein, the term "cell" refers to the meaning as generally recognized in the art. This term is used in its ordinary biological sense, and does not refer to a whole multicellular organism, such as human in particular. The cell may be present in organisms such as birds, plants, and mammals, such as humans, cows, sheep, apes, monkeys, pigs, dogs, and cats. The cell may be prokaryotic (e.g., bacterial cell) or eukaryotic (e.g., mammalian or plant cell). The cell may be of somatic or germline origin, totipotent or pluripotent, divided or non-divided. The cell may also be derived from or may comprise gametes or embryos, stem cells, or fully differentiated cells.

As used herein, the term "pharmaceutical composition" generally refers to a composition suitable for administration to a subject in need thereof. For example, the pharmaceutical composition described herein may comprise the gRNA described herein, the one or more isolated nucleic acid molecule(s) described herein, the donor nucleic acid molecule described herein, and/or the vector described herein, as well as a pharmaceutically acceptable carrier. The term "subject" or "individual" or "animal" or "patient" is used interchangeably herein and refers to a subject (such as mammalian subject) in need of administration of the pharmaceutical composition herein. The animal subject comprises humans, non-human primates, dogs, cats, guinea pigs, rabbits, rats, mice, horses, cattle, cows, and the like, such as mice. In certain embodiments, the pharmaceutical composition may comprise a composition for subretinal, parenteral, transdermal, intracavity, intraarterial, intrathecal, and/or intranasal administration or direct injection into tissue. For example, the pharmaceutical composition is administrated to a subject by injection in the subretinal space.

As used herein, the term "induced pluripotent stem cell" is generally a somatic cell reverted to a cell in the state of totipotency under certain conditions. The totipotency refers to the ability to differentiate into all types of cells in the body and form a complete embryo or further develop into a new individual. For example, as used herein, the induced pluripotent stem cell comprises cells obtained after culture of renal epithelial cells and capable of differentiating into retinal cells.

As used herein, the term "vector" generally refers to a nucleic acid capable of transporting another nucleic acid to which it is linked. One type of vector is "plasmid," which refers to a circular double-stranded DNA loop into which other DNA segments can be ligated, for example, PMD-19T-MCS plasmid constructed as described herein. Another type of vector is "viral vector" in which other DNA segments can be ligated into the viral genome, for example, AAV viral vectors constructed as described herein.

As used herein, the term "CYP4V2" generally refers to a protein that is member 2 of subfamily V of cytochrome P450 family 4. The term "cytochrome P450," also known as CYP450, usually refers to a family of ferroheme proteins, belonging to a class of monooxygenases, and involved in the metabolism of endogenous substances or exogenous substances including drugs and environmental compounds. According to the homology degree of amino acid sequence, the members are divided into three levels: family, subfamily, and individual enzymes. The cytochrome P450 enzyme system may be abbreviated as CYP, wherein the family is represented by Arabic number, the subfamily is represented by English capital letter, and the individual enzyme is represented by Arabic number, such as CYP4V2 herein. The human CYP4V2 gene (HGNC: 23198; NCBI ID: 285440) has a full length of 19.28 kb, located at 4q35, has 11 exons, and plays an important role in fatty acid metabolism (Kumar S., Bioinformation, 2011, 7:360-365). The CYP4V2 described herein may also comprise its functional variants, fragments, homologues, and the like. CYP4V2 is expressed almost in all tissues, but is expressed at a higher level in the retina and retinal pigment epithelium while at a slightly lower level in the cornea tissues. The mutations in the CYP4V2 gene may be associated with Bietti crystalline dystrophy and/or retinitis pigmentosa.

As used herein, the term "gRNA" generally refers to guide RNA, a type of RNA molecule. In nature, crRNA and tracrRNA usually exist as two independent RNA molecules to form gRNA. The term "crRNA," also known as CRISPR RNA, usually refers to a nucleotide sequence complementary to the target DNA to be targeted, and the term "tracrRNA" usually refers to a scaffold RNA capable of binding to the Cas nuclease. The crRNA and tracRNA can also be fused into a single strand. At this time, the gRNA can also be called as single guide RNA (sgRNA). The sgRNA has become the most common form of gRNA used by those skilled in the art in CRISPR technology. Therefore, the terms "sgRNA" and "gRNA" herein may have a same meaning. The sgRNA can be artificially synthesized, or can also be prepared from a DNA template in vitro or in vivo. The sgRNA can bind to the Cas nuclease or can also target the targeted DNA, which can guide the Cas nuclease to cleave the DNA site complementary to the gRNA.

As used herein, the term "HEK293 cell" usually refers to "human embryonic kidney cell 293", which is a cell line derived from human embryonic kidney cells. It has the characteristics of easy culture and high transfection efficiency, and is a very commonly used cell line for studying exogenous genes in the art.

As used herein, the term "renal epithelial cell" generally refers to the epithelial cell of the kidney as collected in human urine. As used herein, it is a source for induced pluripotent stem cells. In the art, the use of renal epithelial cells in urine to induce pluripotent stem cells is cost-effective, versatile, and suitable for all ages, genders, and races. This technique makes obtaining large amounts of patient samples much easier and less expensive than other existing manners.

As used herein, the term "injection in the subretinal space" generally refers to the introduction of the substance to be introduced between the photoreceptor cells and the retinal pigment epithelium (RPE) layer. During the injection in the subretinal space, the injected material (e.g., the gRNA described herein, the one or more isolated nucleic acid molecule(s) described herein, the donor nucleic acid molecule described herein, the vector described herein, as well as a pharmaceutically acceptable carrier) creates a space between there.

In addition to the specific proteins and nucleic acid molecules mentioned herein, the present application may also include functional variants, derivatives, analogs, homologues, and fragments thereof.

The term "functional variant" refers to a polypeptide having substantially the same amino acid sequence or encoded by substantially the same nucleotide sequence as the naturally occurring sequence and capable of possessing one or more activities of the naturally occurring sequence. In the context of this application, a variant of any given sequence refers to a sequence in which a particular sequence of residues (whether amino acid or nucleotide residues) has been modified such that the polypeptide or polynucleotide substantially retains at least one endogenous function. Variant sequences can be obtained by addition, deletion, substitution, modification, replacement, and/or variation of at least one amino acid residues and/or nucleotide residues present in a naturally occurring protein and/or polynucleotide, as long as the original functional activity is retained.

As used herein, the term "derivative" generally refers to the polypeptide or polynucleotide of the present application including any substitution, variation, modification, replacement, deletion, and/or addition of one amino acid residue (or multiple amino acid residues) of the sequence, as long as the resulting polypeptide or polynucleotide substantially retains at least one endogenous function.

As used herein, the term "analog" generally refers to a polypeptide or polynucleotide that includes any mimetic of the polypeptide or polynucleotide, i.e., a chemical compound possessing at least one endogenous function of the polypeptide or polynucleotide which the mimetic mimics.

Generally, the amino acid substitutions, such as at least 1 (e.g., 1, 2, 3, 4, 5, 6, 7, 8, 9, 10, 20, or more) amino acid substitutions, can be made, as long as the modified sequence substantially retains the desired activity or ability. The amino acid substitutions can include the use of non-naturally occurring analogs.

The proteins or polypeptides used herein may also have deletions, insertions, or substitutions of amino acid residues that produce silent changes and result in functionally equivalent proteins. The deliberate amino acid substitutions can be made based on the similarity in polarity, charge, solubility, hydrophobicity, hydrophilicity, and/or amphiphilic nature of the residues, as long as the endogenous function is retained. For example, negatively charged amino acids include aspartic acid and glutamic acid; positively charged amino acids include lysine and arginine; and amino acids containing uncharged polar headgroups with similar hydrophilicity values include asparagine, glutamine, serine, threonine, and tyrosine.

As used herein, the term "homologue" generally refers to an amino acid sequence or nucleotide sequence having a certain homology to the amino acid sequence to be compared and the nucleotide sequence to be compared. The term "homology" can be equivalent to the sequence "identity." A homologous sequence can include an amino acid sequence that is at least 80%, 85%, 90%, 99.1%, 99.2%, 99.3%, 99.4%, 99.5%, 99.6%, 99.7%, 99.8%, or 99.9% identical to the subject sequence. Typically, a homologue will contain the same active site as the subject amino acid sequence and the like. The homology can be considered in terms of similarity (i.e., amino acid residues with similar chemical properties/functions), or it can be expressed in terms of sequence identity. As used herein, a sequence having a percent identity to any of SEQ ID NOs of an amino acid sequence or a nucleotide sequence as mentioned refers to a sequence having said percent identity over the entire length of SEQ ID NO as mentioned.

To determine the sequence identity, the sequence alignment can be performed, which can be performed by various means known to those skilled in the art, for example using BLAST, BLAST-2, ALIGN, NEEDLE, or Megalign (DNASTAR) software, and the like. Those skilled in the art can determine the appropriate parameters for alignment, including any algorithm required to achieve optimal alignment among the full-length sequences to be compared.

In the present application, the term "and/or" should be understood to mean either or both of the options.

As used herein, the term "comprise" or "include" generally means the inclusion of expressly specified features, but without the exclusion of other elements.

As used herein, the term "about" generally refers to variations above or below the specified value within the range of 0.5%-10%, such as variations above or below the specified value within the range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%.

Detailed Descriptions gRNA

In one aspect, the present application provides a gRNA specifically targeting polypeptide 2, subfamily V, family 4, cytochrome P450 (CYP4V2) gene, which specifically binds to the intron region between exon 6 and exon 7 of the CYP4V2 gene.

In certain instances, the gRNA may specifically bind to a nucleotide sequence set forth in SEQ ID NO: 41. In certain instances, the gRNA may specifically bind to a nucleotide sequence having at least 70% (for example, at least 75%, at least 80%, at least 85%, at least 90%, at least 91%, at least 92%, at least 93%, at least 94%, at least 95%, at least 96%, at least 97%, at least 98%, at least 99%, or at least 100%) sequence identity to the nucleotide sequence set forth in SEQ ID NO: 41. In the present application, the "identity" refers to different nucleotide sequences whose base sequences are identical.

In certain instances, the gRNA may specifically bind to a nucleotide sequence complementary to the nucleotide sequence set forth in SEQ ID NO: 41. In certain instances, the gRNA may specifically bind to a nucleotide sequence complementary to the nucleotide sequence having at least 70% (for example, at least 75%, at least 80%, at least 85%, at least 90%, at least 91%, at least 92%, at least 93%, at least 94%, at least 95%, at least 96%, at least 97%, at least 98%, at least 99%, or at least 100%) sequence identity to the nucleotide sequence set forth in SEQ ID NO: 41.

The gRNA described herein may bind to the sequence in the target nucleic acid of interest (e.g., the intron region between exon 6 and exon 7 of the CYP4V2 gene). The gRNA can interact with the target nucleic acid in a sequence-specific manner by hybridization (i.e., base pairing). The nucleotide sequence of the sgRNA may vary depending on the sequence of the target nucleic acid of interest.

In the present application, the gRNA may comprise a nucleotide sequence set forth in any of SEQ ID NOs: 48-51. In the present application, the gRNA may comprise a nucleotide sequence having at least 70% (for example, at least 75%, at least 80%, at least 85%, at least 90%, at least 91%, at least 92%, at least 93%, at least 94%, at least 95%, at least 96%, at least 97%, at least 98%, at least 99%, or at least 100%) sequence identity to the nucleotide sequence set forth in any of SEQ ID NOs: 48-51.

In the present application, the gRNA may comprise from 5' to 3': (X)n, a nucleotide sequence set forth in any of SEQ ID NOs: 48-51, and a skeleton sequence, wherein X is a base selected from any of A, U, C, and G, and n is any integer from 0 to 15. In the present application, the gRNA may comprise 5'-(X)n-nucleotide sequence set forth in any of SEQ ID NOs: 48-51-skeleton sequence-3', wherein X is a base selected from any of A, U, C, and G, and n is any integer from 0 to 15.

Figure 4:
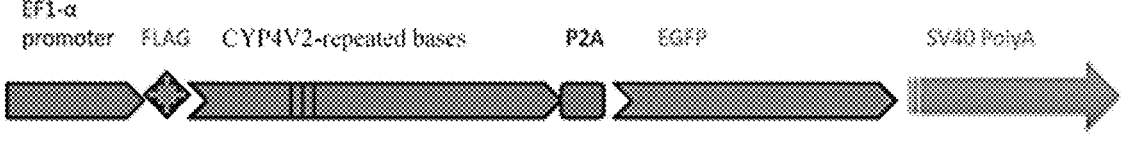
FIG. 4 shows the map of the minigene fragments described in the present application.

For example, the skeleton sequence described herein generally refers to other parts of the gRNA other than those that recognize or hybridize the target sequence, and may comprise the sequence between the gRNA pairing sequence and the transcription terminator in the sgRNA. Generally, the skeleton sequence does not change with the target sequence, nor does it affect the recognition of the target sequence by the gRNA. Thus, the skeleton sequence may be any feasible sequence in the prior art. The structure of the skeleton sequence can be found in the parts other than the spacer sequences described in panels A and B of FIG. 1, panels A, B, and C of FIG. 3, as well as panels A, B, C, D, and E of FIG. 4 in the literature Nowak et al. Nucleic Acids Research 2016. 44:9555-9564.

In certain instances, the gRNA may be a single-stranded or double-stranded guide RNA. For example, the gRNA may be a single-stranded guide RNA (e.g., sgRNA).

The present application provides one or more isolated nucleic acid molecule(s) that can encode the gRNA specifically targeting the CYP4V2 gene described above. For example, the isolated nucleic acid molecule may comprise a nucleotide sequence set forth in any of SEQ ID NOs: 1-7.

The present application provides one or more isolated nucleic acid molecule(s) that can encode the gRNA specifically targeting the CYP4V2 gene described above. For example, the isolated nucleic acid molecule may comprise a nucleotide sequence set forth in any of SEQ ID NOs: 1-4.

In the present application, the gRNA sequence may be designed to hybridize to a target nucleic acid in the vicinity of a PAM sequence recognizable by the Cas nuclease. The gRNA may be completely complementary to the target sequence, or may be incompletely complementary to the target sequence. The degree of complementarity between the gRNA and its corresponding target sequence is at least 50% (e.g., at least about 55%, about 60%, about 65%, about 70%, about 75%, about 80%, about 85%, about 90%, about 95%, about 98%, or more). The "Cas nuclease" generally refers to the ability to use a CRISPR sequence (e.g., gRNA) as a guide to recognize and cleave a specific DNA strand, for example, Cas9 nuclease, Csn1 or Csx12. The Cas9 nuclease typically includes a RuvC nuclease domain and an HNH nuclease domain, which cleave two different strands of a double-stranded DNA molecule, respectively. The Cas9 nuclease has been described in different bacterial species such as *S. thermophiles, Listeria innocua* (Gasiunas, Barrangou et al. 2012; Jinek, Chylinski et al. 2012), and *S. pyogenes* (Deltcheva, Chylinski et al. 2011). For example, the amino acid sequence for *Streptococcus pyogenes* Cas9 protein can be found in SwissProt database with accession number Q99ZW2; the amino acid sequence for *Neisseria meningitides* Cas9 protein can be found in UniProt database with number A1IQ68; the amino acid sequence for *Streptococcus thermophilus* Cas9 protein can be found in UniProt database with number Q03LF7; and the amino acid sequence for *Staphylococcus aureus* Cas9 protein (e.g., SaCas in the vector described herein) can be found in UniProt database with number J7RUA5. The Cas nuclease may usually recognize a specific PAM sequence in the DNA. For example, the PAM may comprise a nucleotide sequence set forth in any of SEQ ID NOs: 8-14.

The gRNA and/or isolated nucleic acid molecule described herein may be delivered using a vector. In the present application, the vector (such as pX601) may or may not contain a nucleic acid encoding the Cas nuclease. In the present application, the Cas nuclease may be delivered individually as one or more polypeptides. Alternatively, the nucleic acid molecule encoding the Cas nuclease as well as one or more guide RNAs, or one or more crRNAs and tracrRNAs are delivered individually or pre-complexed together for delivery. For example, the nucleic acid molecule of the present application (e.g., the isolated nucleic acid molecule encoding the sgRNA specifically targeting the CYP4V2 gene) and the nucleic acid molecule encoding the Cas9 nuclease may be located in a same vector (e.g., a plasmid). The vector may include viral or non-viral vectors known in the art.

The non-viral delivery vector may include, but not limited to, nanoparticles, liposomes, ribonucleoproteins, positively charged peptides, small-molecule RNA conjugates, aptamer-RNA chimeras, and RNA fusion protein complexes.

In the present application, the isolated nucleic acid molecule and/or the nucleic acid molecule encoding a DNA endonuclease may be delivered via a plasmid.

In certain instances, the vector may be a viral vector, e.g., AAV, lentivirus, retrovirus, adenovirus, herpes virus, and hepatitis virus. The methods for producing the viral vector comprising the nucleic acid molecule (e.g., isolated nucleic acid molecule described herein) as part of the vector genome are well known in the art and may be performed by those skilled in the art without undue experimentation. In other instances, the vector may be a recombinant AAV virion that packages the nucleic acid molecule described herein. The methods for producing a recombinant AAV may include introducing the nucleic acid molecule described herein into a packaging cell line, introducing a packaging plasmid expressing the AAV rep and cap genes into the cell line, and collecting the recombinant AAV from the supernatant of the packaging cell line. Various types of cells may be used as packaging cell lines. For example, the packaging cell lines that can be used include, but are not limited to, HEK 293 cells, HeLa cells, and Vero cells.

Donor Nucleic Acid Molecule and Vector

In another aspect, the present application also provides a donor nucleic acid molecule. In the present application, the term "donor nucleic acid molecule" generally refers to a nucleic acid molecule that provides a heterologous nucleic acid sequence to a recipient (e.g., receiving the nucleic acid molecule). In certain instances, the donor nucleic acid molecule is introduced into a recipient cell, and the DNA fragments (e.g., double-stranded DNA after breakage) that have been cleaved by the isolated nucleic acid molecule may be repaired. In some other instances, the DNA breakage may be repaired by the donor nucleic acid molecule. The repairing manner includes, but not limited to, homologous recombination (HR) repair dependent upon DNA homology and non-homologous end joining (NHEJ) repair. HR uses the homologous sequence or donor sequence as a template to insert a specific DNA sequence at the breakpoint. The homologous sequence may be in the endogenous genome, such as sister chromatid. Alternatively, the donor may be an exogenous nucleic acid, such as plasmid, single-stranded oligonucleotide, double-stranded oligonucleotide, or virus. For example, the donor may comprise the donor nucleic acid molecule described herein. These exogenous nucleic acids may comprise regions of high homology to Cas nuclease-cleavable locus, and may also comprise additional sequences or sequence changes (including deletions that can be incorporated into the cleavable target locus). NHEJ directly joins the ends of DNA resulted from double-strand breakages, sometimes missing or adding nucleotide sequences, which may disrupt or enhance the gene expression; for example, NHEJ-based microhomology-mediated end joining (MMEJ), homology-independent targeted integration (HITI), and HR-mediated homology-mediated end joining (HMEJ). For example, in the present application, by using the HITI repair manner, the donor nucleic acid molecule is ligated to the DNA fragment (e.g., CYP4V2 gene fragment) after the cleavage by the isolated nucleic acid molecule (e.g., the isolated nucleic acid molecule encoding the sgRNA specifically targeting the CYP4V2 gene).

The donor nucleic acid molecule described herein may be a wild-type human nucleotide sequence or a gene fragment containing different numbers of introns and exons. In certain instances, the donor nucleic acid molecule may or may not contain introns (0, 1, 2, 3, 4, 5, 6, 7, 8, 9, 10, or 11). In certain instances, it may comprise a nucleotide sequence between intron 6 and exon 11 of CYP4V2 gene. For example, it may comprise a nucleotide sequence of one or more (e.g., 2, 3, 4, 5, or 6) exons between intron 6 and exon 11, for example may comprise one or more nucleotide sequences of exon 7, exon 8, exon 9, exon 10, and/or exon 11. For example, in the present application, the donor nucleic acid molecule may comprise exons 7 to 11 of CYP4V2. For example, the donor nucleic acid molecule comprises a nucleotide sequence set forth in SEQ ID NO: 39. In certain instances, the donor nucleic acid may comprise a nucleotide sequence having at least 70% (for example, at least 75%, at least 80%, at least 85%, at least 90%, at least 91%, at least 92%, at least 93%, at least 94%, at least 95%, at least 96%, at least 97%, at least 98%, at least 99%, or at least 100%) sequence identity to the nucleotide sequence set forth in SEQ ID NO: 39. The "nucleic acid molecule" described herein that may comprise a CYP4V2 nucleotide sequence is different from the gRNA specifically targeting CYP4V2 or the "isolated nucleic acid molecule" described herein.

In another aspect, the present application provides a vector, comprising the isolated nucleic acid molecule (e.g., an isolated nucleic acid molecule encoding the sgRNA specifically targeting the CYP4V2 gene) and/or the donor nucleic acid molecule (e.g., a nucleotide molecule encoding the human CYP4V2 gene).

In certain instances, the isolated nucleic acid molecule and the donor nucleic acid molecule may be located in different vectors. In some other instances, the isolated nucleic acid molecule and the donor nucleic acid molecule may be located in a same vector. In the present application, after the vector containing the isolated nucleic acid molecule and the vector containing the donor nucleic acid molecule are simultaneously introduced into a cell, the Cas nuclease may simultaneously cleave the donor nucleic acid molecule and the genomic DNA of the cell, and integrate the donor nucleic acid molecule into the precise site (e.g., CYP4V2 gene fragment) in the cell genome. In certain instances, the integration efficiency of this process is very high.

In certain embodiments, the vector is a viral vector; for example, AAV, lentivirus, retrovirus, adenovirus, herpes virus, and hepatitis virus. The methods for producing the viral vector comprising the nucleic acid molecule (e.g., isolated nucleic acid molecule described herein) as part of the vector genome are well known in the art and may be performed by those skilled in the art without undue experimentation.

Cell, Pharmaceutical Composition, Use, and Method

The present application provides a cell, which may comprise the isolated nucleic acid molecule and/or the donor nucleic acid molecule. The cell described herein may express sgRNA and Cas nuclease, and have a good DNA cleavage effect. The cell described herein may also express the CYP4V2 protein with a normal function. The cell may include mammalian cells, e.g., cells from humans. For example, the cell may include COS cells, COS-1 cells, Chinese Hamster Ovary (CHO) cells, HeLa cells, HEK293 cells, NSO cells or myeloma cells, stem cells (e.g., pluripotent stem cells and/or totipotent stem cells), and/or epithelial cells (e.g., kidney epithelial cells and/or retinal epithelial cells). In the present application, the cell may include HEK293T cells and/or urine kidney epithelial cells. In the present application, the cells may be modified to have a differentiation potential. The differentiation potential may include the potential to differentiate into any cell type in the body: neurons, astrocytes, oligodendrocytes, retinal epithelial cells, epidermis, hair and keratinocytes, hepatocytes, pancreatic beta cells, intestinal epithelial cells, alveolar cells, hematopoietic cells, endothelial cells, cardiomyocytes, smooth muscle cells, skeletal muscle cells, kidney cells, adipocytes, chondrocytes, and/or osteocytes. For example, the cell may be reprogrammed into induced pluripotent stem cells (iPSCs) with key reprogramming genes (e.g., OCT4, KLF4, SOX2, cMYC, NANOG, and/or LIN28) overexpressed.

The cell described herein may be used to evaluate the effectiveness and safety of a substance required for gene editing therapy (e.g., sgRNA and donor nucleic acid molecule).

The present application provides a pharmaceutical composition comprising the gRNA, the one or more isolated nucleic acid molecule(s), the donor nucleic acid molecule, or the vector, and a pharmaceutically acceptable carrier. The carrier should be nontoxic, and should not interfere with the efficacy of the active ingredient.

The present application provides a kit. The kit generally comprises two or more components packaged together in a container, receptacle, or other containers; for example, the gRNA, the one or more isolated nucleic acid molecule(s), the donor nucleic acid molecule, and the vector as described herein.

The pharmaceutical composition described herein may be introduced by a variety of methods, for example, including but not limited to, intravitreal injection (e.g., anterior, medial, or posterior vitreous injection), subconjunctival injection, intracameral injection, bitamporal injection into anterior chamber, intrastromal injection, injection into the subchoroidal space, intracorneal injection, subretinal injection, and locally administration to eyes via intraocular injection. The introduction may comprise the subretinal injection, that is, injection into the subretinal space, i.e., beneath the neurosensory retina. During the subretinal injection, the injected material (e.g., the targeting vector, the gRNA, and/or the plasmid) is directly introduced between the photoreceptor cells and the retinal pigment epithelium (RPE) layer, and creates a space between there.

The present application provides the use of the gRNA, the one or more isolated nucleic acid molecule(s), the donor nucleic acid molecule, and/or the vector in the manufacture of a medicament for treating a disease. Among them, the disease may include a disease caused by CYP4V2 gene mutations. Among them, the mutation is located behind the intron between exon 6 and exon 7 of the CYP4V2 gene. For example, the disease may include Bietti crystalline dystrophy.

The present application provides a method for treating the Bietti crystalline dystrophy, comprising the following steps: introducing the gRNA (e.g., sgRNA specifically targeting CYP4V2 gene), the one or more isolated nucleic acid molecule(s) (the isolated nucleic acid molecule encoding the sgRNA specifically targeting CYP4V2 gene), the donor nucleic acid molecule (the nucleotide molecule encoding human CYP4V2 gene), and/or the vector into a subject in need thereof. Among them, the introduction enables the subject to obtain a CYP4V2 protein with a normal function.

The method described herein may include an ex vivo method. In certain instances, the subject-specific induced pluripotent stem cells (iPSCs) may be obtained. Then, the induced pluripotent stem cells may be differentiated into any type of cells, such as photoreceptor cells or retinal progenitor cells. In the present application, it may be a 3D retinal organoid. Next, the genomic DNA of these 3D retinal organoid cells may be edited using the method described herein. For example, this method may include editing in or near the mutation site of the CYP4V2 gene of the 3D retinal organoid cell, such that it does not encode a CYP4V2 protein with mutations. Finally, the 3D retinal organoid cells may be implanted into the subject.

In other instances, the photoreceptor cells or retinal progenitor cells may be isolated from the subject. Next, the genomic DNA of these photoreceptor cells or retinal progenitor cells may be edited using the method described herein. For example, this method may include editing in or near the mutation site of the CYP4V2 gene of the photoreceptor cell or retinal progenitor cell, such that it does not have mutated CYP4V2. Finally, the gene-edited photoreceptor cells or retinal progenitor cells may be implanted into the subject.

The method may comprise a comprehensive analysis of the therapeutic agent prior to administration. For example, the entire genome of the corrected cell is sequenced to ensure that no off-target effects, if any, can be at the genomic positions associated with minimal risk to the subject. Moreover, a population of specific cell (including clonal cell population) may be isolated prior to implantation.

The method described herein may comprise the process for cleaving DNA at a precise target position in the genome using a site-directed nuclease, thereby producing single- or double-stranded DNA breakages at the specific position within the genome. Such breakages may be regularly repaired by endogenous cellular processes such as homologous recombination and non-homologous end joining.

The methods described herein may comprise creating one DNA breakage, or two DNA breakages which may be double-stranded breakages or two single-stranded breakages, at the position near the target sequence in the target locus. The breakage may be achieved by a site-directed polypeptide. The site-directed polypeptide (e.g., DNA endonuclease) can introduce double- or single-stranded breakages in the nucleic acid (e.g., genomic DNA). The double-stranded breakage can stimulate the endogenous DNA repair pathway in a cell, such as HR and NHEJ.

Using an exogenous donor template, additional nucleic acid sequences (e.g., the targeting vector) or modifications (e.g., single or multiple base changes or deletions) may be introduced between homologous flanking regions, such that the additional or changed nucleic acid sequences are incorporated into the loci of interest. The exogenous donor may be delivered by a plasmid vector, for example, AAV vector and/or TA cloning vector (e.g., ZT4 vector).

The present application provides a method for regulating the expression of CYP4V2 gene in cells, comprising introducing the gRNA, the one or more isolated nucleic acid molecule(s), and/or the vector into the cells.

The method described herein may involve introducing the gRNA into the cell. For example, the gRNA targets the CYP4V2 gene fragment in the genome of the recipient cell, and cleaves it with the help of nuclease, thereby producing the effects that the chances of the CYP4V2 gene being translated into proteins are reduced and the translated proteins cannot perform a normal function.

The methods described herein may involve introducing the one or more isolated nucleic acid molecule(s) into the cell. For example, the isolated nucleic acid molecule encoding the sgRNA specifically targeting CYP4V2 gene destroys the CYP4V2 gene fragment, thereby producing the effects that the chances of the CYP4V2 gene being translated into proteins are reduced and the translated proteins cannot perform a normal function.

The method described herein may involve introducing the vector into the cell. The vector comprises the isolated nucleic acid molecule and/or the donor nucleic acid molecule. In certain instances, the vector contains the isolated nucleic acid molecule and the donor nucleic acid molecule, such that the CYP4V2 gene in the cell is replaced by the donor nucleic acid molecule, thereby producing the effects that the chances of the CYP4V2 gene being translated into proteins are changed (for example, from the absence of CYP4V2 protein expression to normal expression) and the abnormal function of the translated proteins is changed to a normal function. In certain instances, the vector contains the isolated nucleic acid molecule such that the CYP4V2 gene fragment is destroyed, thereby producing the effects that the chances of the CYP4V2 gene being translated into proteins are reduced and the translated proteins cannot perform a normal function. In other instances, the vector contains the donor nucleic acid molecule, such that the cell contains more CYP4V2 gene fragments, and more CYP4V2 proteins can be transcribed and translated.

Without intention to be limited by any theory, the following Examples are only intended to illustrate the nucleic acid molecules, preparation methods, uses, etc. in the present application, and are not intended to limit the scope of the claimed invention.

EXAMPLES

Example 1. SgRNA Design

I. SgRNA Screening

According to the DNA sequence of CYP4V2 gene, a sgRNA was designed with PAM sequence of NNGRRT and NNGRR (*Staphylococcus aureus*, SA; SaCas9) and a length of 21 bp in the intron region between exon 6 and exon 7 of CYP4V2.

According to the scores, a total of 7 sgRNAs (5 for NNGRRT and 2 for NNGRR) were designed, and their sequences were shown in Table 1.

TABLE 1

| | | | | Specificity | Efficiency |
|---|---|---|---|---|---|
| | Strand | Sequence | PAM | Score | Score |
| sgRNA1 | 1 | CTGGGCTCTAGGAATTC CACC (SEQ ID NO: 1) | AAGAAT (SEQ ID NO: 8) | 83 | 64 |
| sgRNA2 | −1 | CATAGGCTCCATAGTCC TACA (SEQ ID NO: 2) | CCGGGT (SEQ ID NO: 9) | 89 | 39 |
| sgRNA3 | 1 | CAGAAATCGCAAGCATA GAGG (SEQ ID NO: 3) | GTGAAT (SEQ ID NO: 10) | 78 | 55 |
| sgRNA4 | −1 | GCAGTCTTTCCAACACA AGAA (SEQ ID NO: 4) | TAGAAT (SEQ ID NO: 11) | 71 | 44 |

Table title (above): CYP4V2-HITI benchling online design of the nucleic acid molecules encoding sgRNAs TABLE 1-continued

| | | CYP4V2-HITI benchling online design of the nucleic acid molecules encoding sgRNAs | | | |
|---|---|---|---|---|---|
| | Strand | Sequence | PAM | Specificity Score | Efficiency Score |
| sgRNA5 | 1 | AGTGTGATCACCTGGTT ATAG (SEQ ID NO: 5) | GAGAAT (SEQ ID NO: 12) | 91 | 18 |
| sgRNA6 | -1 | AAAAGTTCTGGAAATGA ACGG (SEQ ID NO: 6) | TGGGG (SEQ ID NO: 13) | 79 | 56 |
| sgRNA7 | 1 | TGTATATGGTCCGTACC TGAA (SEQ ID NO: 7) | AGGAA (SEQ ID NO: 14) | 90 | 61 |

II. SgRNA Synthesis

According to the sequence of digestion site Bbs1, the Bbs1 digestion sites were added in the upstream and downstream of the designed sgRNA; and the corresponding primers were designed within 400 bp upstream and downstream of each sgRNA. The correspondingly designed oligonucleotide sequences and primers were shown in Table 2.

TABLE 2

| | | SgRNA design | |
|---|---|---|---|
| No. | Sequence | | Correspondingly designed upstream and downstream primers |
| CYP4V2sgRNA1 | 1-F: CACCGCTGGGCTCTAGGAATTC CACC (SEQ ID NO: 15) 1-R: AAACGGTGGAATTCCTAGAGCC CAGC (SEQ ID NO: 16) | | P1-F: TGGAGTTATGTCCTTGTGGTG (SEQ ID NO: 29) P1-R: CCTGCTACTAAGTGGCCTGAA (SEQ ID NO: 30) |
| CYP4V2sgRNA2 | 2-F: CACCGCATAGGCTCCATAGTCC TACA (SEQ ID NO: 17) 2-R: AAACTGTAGGACTATGGAGCCT ATGC (SEQ ID NO: 18) | | P2.6-F: CGTCATTCCCACGATTGCCT (SEQ ID NO: 31) P2.6-R: TGGTGGTTAGCACTTAGCGAG (SEQ ID NO: 32) |
| CYP4V2sgRNA3 | 3-F: CACCGCAGAAATCGCAAGCATA GAGG (SEQ ID NO: 19) 3-R: AAACCCTCTATGCTTGCGATTTC TGC (SEQ ID NO: 20) | | P3.4-F: AAGCATGGCAGTGTTTGAGTT G (SEQ ID NO: 33) P3.4-R: CGTTCATTTCATTGGCCCGT (SEQ ID NO: 34) |
| CYP4V2sgRNA4 | 4-F: CACCGGCAGTCTTTCCAACACA AGAA (SEQ ID NO: 21) 4-R: AAACTTCTTGTGTTGGAAAGAC TGCC (SEQ ID NO: 22) | | P3.4-F: AAGCATGGCAGTGTTTGAGTT G (SEQ ID NO: 33) P3.4-R: CGTTCATTTCATTGGCCCGT (SEQ ID NO: 34) |
| CYP4V2sgRNA5 | 5-F: CACCGAGTGTGATCACCTGGTT ATAG (SEQ ID NO: 23) 5-R: AAACCTATAACCAGGTGATCAC ACTC (SEQ ID NO: 24) | | P5-F: CGGCAGTCATTTTCAAAGGCA (SEQ ID NO: 35) P5-R: CAGGCCTCAGTAGGCAATTCT (SEQ ID NO: 36) |
| CYP4V2sgRNA6 | 6-F: CACCGAAAAGTTCTGGAAATGA ACGG (SEQ ID NO: 25) 6-R: AAACCCGTTCATTTCCAGAACTT TTC (SEQ ID NO: 26) | | P2.6-F: CGTCATTCCCACGATTGCCT (SEQ ID NO: 31) P2.6-R: TGGTGGTTAGCACTTAGCGAG (SEQ ID NO: 32) |

TABLE 2-continued

SgRNA design

| No. | Sequence | Correspondingly designed upstream and downstream primers |
|-----|----------|------------------------------------------------------------|
| CYP4V2sgRN A7 | 7-F: CACCGTGTATATGGTCCGTACCT GAA (SEQ ID NO: 27) 7-R: AAACTTCAGGTACGGACCATAT ACAC (SEQ ID NO: 28) | P7-F: ACCAACAGTGTAAGTCCCTGA (SEQ ID NO: 37) P7-R: ACACAGCACCCTGTTTGTTC (SEQ ID NO: 38) |

III. The Detailed Protocols for sgRNA Vector Construction and Plasmid Extraction Were as Follows 1. The synthesized sgRNA was annealed in accordance with the following protocols.

The forward primer (F) and reverse primer (R) synthesized as above for each sgRNA were diluted to 50 μmol, respectively. 5 μl of each sgRNA (F, R) was used to prepare sgRNA mixtures 1-7. T4 polynucleotide kinase (PNK) and 10×T4 Ligation Buffer were thawed on ice for later use. The following reaction system was prepared:

| | |
|---|---|
| SgRNA mix | 7 μl |
| 10 × T4 Ligation Buffer | 1 μl |
| T4 polynucleotide kinase | 2 μl |
| Total volume | 10 μl |

The reaction system prepared as above was placed in a PCR instrument, and the following reaction program was run:

| | |
|---|---|
| 37° C. | 30 min |
| 95° C. | 5 min |
| Ramp down to 25° C. at 5° C. /min | Forever |
| 25° C. | |

The reaction product was recovered.

2. The protocols for vector digestion were as follows.

The plasmid used to construct the sgRNA vector was pX601 vector (Addgene, 61591). The plasmid map was shown in FIG. 1.

BSaI digestion was used to release the binding site for sgRNA. The following digestion reaction system was prepared in a 1.5 ml PCR tube:

| | |
|---|---|
| Plasmid (15 μg) | 15 μl |
| 2x Cutsmart ™ Buffer | 30 μl |
| Enzyme | 12 μl |
| Water | ad 258 μl |
| Total volume | 300 μl |

After digestion for 1-2 h (or digestion overnight), the system was recovered and purified. The concentration was determined, and then it was diluted to 50 ng/μl.

3. The sgRNA was ligated to the vector recovered in step 2.

The recovered vector from step 2 and the annealed sgRNA were used to prepare the following ligation system (200 μl PCR tube):

| | |
|---|---|
| Digestion vector | 1 μl |
| Annealed sgRNA | 1 μl |
| 2x T4 Ligation Buffer | 5 μl |
| T4 Ligase | 1 μl |
| H₂O | 3 μl |
| Total volume | 11 μl |

The ligation reaction system was placed at 37° C. for about 1-2 hours to complete the sgRNA vector construction.

4. Plasmid transformation (1) TransStbl3 competent cells (TransGen Biotech, CD-521-02) were placed on ice for thawing;

(2) 1 μl of ligation product was added to 50 μl of competent cells, and incubated on ice for half an hour, subjected to heat shock at 42° C. for 90 s, and kept on ice for 2 min;

(3) 500 μl of antibiotic-free medium was added at 37° C. and shaken at 200 rpm for 1 h;

(4) The system was centrifuged at 800 rpm/min for 5 min, and the supernatant was discarded for remaining about 100 μl. The LB agar medium containing ampicillin was used to screen positive clones;

(5) On the next day, the positive colony was picked (500 μl of medium) and shaken for 3-4 hours, 200 μl of which was sent for sequencing.

5. Plasmid extraction (in accordance with Omega Endo-toxin-free Plasmid Maxiprep Kit)

(1) Seven plasmids in total (pX601-SaCas9-CYP4V2-SgRNA1-7) validated by sequencing were shaken over-night (50-200 mL), and incubated on a shaker at 37° C. for 12-16 h to amplify the plasmid, and extracted on the next day (shaking for less than 16 h).

(2) 50-200 mL of bacteria was centrifuged at 4,000×g for 10 min at room temperature, to collect the bacterial cells.

(3) The medium was discarded. 10 mL of Solution I/RNase A mixture was added to the pellet, and the cells were completely resuspended by pipetting or vortexing.

(4) 10 mL of Solution II was added. The centrifuge tube was capped and gently inverted for 8-10 times to obtain a clear lysate. If necessary, the lysate was left to stand at room temperature for 2-3 minutes.

(5) 5 mL of pre-chilled N3 Buffer was added. The centrifuge tube was capped and gently inverted for 10 times until a white flocculent precipitate was formed. The system may be left to stand and incubated at room temperature for 2 min.

(6) A syringe filter was prepared. The plunger in the syringe was pulled out. Then the syringe was vertically placed on a suitable test-tube support, and a collection tube was placed at the outlet of the lower end of the syringe, with the opening of the syringe faced upward.

The lysate was immediately poured into the syringe of the filter. The cell lysate was remained in the syringe for 5 min. At this time, white floccules would float on the surface of the lysate. The cell lysate may have flowed out of the filter syringe port. The cell lysate was collected in a new 50 mL tube. The plunger of the syringe was carefully and gently inserted into the syringe, and pushed slowly such that the lysate flowed into the collection tube.

(7) One-tenth volume of ETR Solution (blue) was added to the filtered lysate that had flowed out. The tube was inverted for 10 times, and then left to stand in an ice bath for 10 minutes.

(8) The above lysate was kept in water bath at 42° C. for 5 min. The lysate would be cloudy again. At this time, the lysate was centrifuged at 4,000×g for 5 minutes at 25° C. The ETR Solution would form a blue layer at the bottom of the tube.

(9) The supernatant was transferred to another new 50 mL tube, and a half volume of absolute ethanol at room temperature was added. The tube was gently inverted for 6-7 times, and placed at room temperature for 1-2 min.

(10) A HiBind® DNA Maxi binding column was cased in a 50 mL collection tube, and 20 mL of filtrate was added to the HiBind® DNA Maxi binding column, for centrifuging at 4,000×g for 3 min at room temperature. The filtrate was discarded.

(11) The HiBind® DNA Maxi binding column was cased in the same collection tube to repeat the step 10) until all the remaining filtrate was bound to the HiBind® DNA Maxi binding column, for centrifuging under the same conditions.

(12) The HiBind® DNA Maxi binding column was cased in the same collection tube, and 10 mL of HBC Buffer was added to the HiBind® DNA Maxi binding column, for centrifuging at 4,000×g for 3 min at room temperature. The filtrate was discarded.

(13) The HiBind® DNA Maxi binding column was cased in the same collection tube, and 15 mL of DNA Wash Buffer (diluted with absolute ethanol) was added to the HiBind® DNA Maxi binding column, for centrifuging at 4,000×g for 3 min at room temperature. The filtrate was discarded.

(14) The HiBind® DNA Maxi binding column was cased in the same collection tube, and 10 mL of DNA Wash Buffer (diluted with absolute ethanol) was added to the HiBind® DNA Maxi binding column, for centrifuging at 4,000×g for 3 min at room temperature. The filtrate was discarded.

(15) The matrix of the HiBind® DNA Maxi binding column was dried by centrifuging in an empty state at maximum speed (not exceeding 6,000×g) for 10 minutes.

(16) (Optional) The HiBind® DNA Maxi binding column was further air-dried. One of the following processes was (optionally) chosen to further dry the HiBind® DNA Maxi binding column before the elution of DNA (if necessary):

a) The HiBind® DNA Maxi binding column was placed in a vacuum container for 15 min to dry the ethanol: the column was moved to the vacuum chamber at room temperature and all vacuum chamber devices were connected. The vacuum chamber was sealed and vacuumed for 15 min. The HiBind® DNA Maxi binding column was removed for the next operation. b) The column was dried in a vacuum oven or at 65° C. for 10 to 15 min. The HiBind® DNA Maxi binding column was removed for the next operation.

(17) The HiBind® DNA Maxi binding column was placed in a clean 50 mL centrifuge tube, 1-3 mL of endotoxin-free Elution Buffer was directly added onto the HiBind® DNA Maxi binding column matrix (the amount added depending on the expected final product concentration), and left to stand at room temperature for 5 min.

(18) The DNA was eluted by centrifuging at 4,000×g for 5 min.

(19) The column was discarded, and the DNA product was stored at −20° C.

(20) The extracted plasmids pX601-SaCas9-CYP4V2-SgRNA1 to pX601-SaCas9-CYP4V2-SgRNA7 was sequenced again to ensure that the constructed plasmids were correct.

IV. Validation of sgRNA Effectiveness in 293T Cells 1. 293T Cell Culture (1) Thawing of Frozen Cells a) The temperature of the thermostatic water bath was adjusted to 37° C. The frozen cells were taken out from the liquid nitrogen. By clamping the lid with tweezers, the container was shaken quickly in the water.

b) The liquid was transferred to a 15 ml centrifuge tube, 10 ml of culture medium was slowly added, and shaken gently to homogenize the liquid. After tightening the lid, the tube was centrifuged at 1,000 rpm/min for 3 min.

c) Removing the supernatant and adding an appropriate amount of medium. The cell at the bottom was pipetted gently, and then the cells were transferred to a culture flask for culturing in an incubator. 293T cells were cultured at 37° C. with 5% $CO_2$, using high-glucose DMEM supplemented with 10% fetal bovine serum and 100 U/ml penicillin/streptomycin as the medium.

(2) Cell Passage a) The morphology and density of the cells were observed under an inverted microscope. When the cells in the culture flask reached 80%-90% confluence, the cells were passaged.

b) The old medium in the cell culture flask was washed out, and the flask was washed with PBS for 3 times. 500 μl of EDTA-containing trypsin was added to the culture flask, and incubated for about 1 min in the incubator. When the intercellular space became larger and the cells became round, 1 ml of medium was immediately added to the culture flask to stop the digestion. The cells were pipetted gently, and after all the cells floated from the bottom of the flask, the liquid in the culture flask was transferred to a centrifuge tube and centrifuged at 1,000 rpm/min for 2 min.

c) The supernatant was discarded, and 2 ml of medium was added to the centrifuge tube to resuspend the cells. The cell suspension was dispensed into 4 new culture flasks, and 4 ml of medium was added to each flask. The culture flask was shaken gently such that the cells were mixed evenly and plated onto the culture flask, and then placed into a cell incubator for culturing.

d) On the day before transfection, 293T cells (100 w) having a density of 80%, under cell stretching, and with uniform intercellular space were added to each well, and subjected to plasmid transfection when the cells reached 80-90% confluence on the next day.

2. 293T Cell Transfection by Polyethyleneimine (PEI) Method (1) 1.5 mL EP tubes were taken. 250 μL of DMEM medium (serum-free) was added to each tube, and 1.5 μg of pX601-CYP4V2-sgRNA1 plasmid and 1 μg of pLent-GFP plasmid were successively added (co-transfection, for roughly marking whether the pX601-CYP4V2-sgRNA1 plasmid was transferred therein). After mixing well by vortexing, 7.5 μL of PEI transfection reagent was added to each tube, mixed well by vortexing, and left to stand at room temperature for 20 min before transfection. In the same way, pX601-CYP4V2-sgRNA2 to pX601-CYP4V2-sgRNA7 plasmid transfection systems, pX601 empty plasmid transfection system, and blank control were added to other wells in the 6-well plate, respectively.

(2) The system was dropwise added to the culture medium (the culture medium in 6-well plate plus serum-free DMEM=2 ml/well), cultured in an incubator, and half of the medium was refreshed within 12-18 hours. On the next day, the GFP expression was observed under a fluorescence microscope to assess the transfection efficiency, and the transfected plasmid was continued to be cultured if the transfection efficiency was good.

(3) Screening of Resistant Cells a) Solution formulation: 10 mg/ml (mother solution) puromycin was diluted to 1 μg/ml puromycin for cell screening.

b) Medium changing: two days after transfection, 3 ml of 293T cell medium containing puromycin was added to each well (including the negative control group) to screen for transfected positive cells. Then the survival state of the cells was observed every day. The culture medium was refreshed every 2 days, and a corresponding amount of puromycin was added when changing the medium. At the time that the cells in the negative control well were completely dead while the experimental group and the control group had viable cells (indicating successful transfection), the antibiotic screening was terminated and the culture medium was changed to the normal medium.

3. Extraction of Genomic DNA From 293T Cells (1) After the cells in the 6-well plate reached 80-90% confluence, the cells were passaged to a 6 cm culture dish.

(2) After the cells reached 80-90% confluence, the cells were harvested for extracting the genomic DNA. The whole process lasted for about 7-10 days. The genomic DNA was extracted using the cell extraction kit from Vazyme Biotech, and the experimental protocols were as follows:

a) The cells were collected by centrifugation at 400×g for 5 min, and the supernatant was discarded. 220 μl of phosphate buffer solution (PBS), 10 mL of RNase Solution, and 20 μL of PK working solution were added to the sample. The cells were resuspended, and left to stand at room temperature for more than 15 min.

b) 250 μl of Buffer GB was added to the cell resuspension, mixed well by vortexing, placed in water bath at 65° C. for 15-30 min, and purified by column;

c) 250 μl of absolute ethanol was added to the digestion solution, and mixed well by vortexing for 15-20 s;

d) The gDNA adsorption column was placed in a 2 ml collection tube. The mixture liquid obtained in the above step (including the precipitate) was transferred to the adsorption column, and centrifuged at 12,000×g for 1 min. If the column plugging occurred, the column was centrifuged at 14,000×g for 3-5 min. If the mixture liquid exceeded 750 μL, it was necessary to pass through the column in fractions.

e) The filtrate was discarded, and the adsorption column was placed in the collection tube. 500 μl of Washing Buffer A was added to the adsorption column, and centrifuged at 12,000×g for 1 min.

f) The filtrate was discarded, and the adsorption column was placed in the collection tube. 650 μl of Washing Buffer B was added to the adsorption column, and centrifuged at 12,000×g for 1 min.

g) Step 4 was repeated.

h) The filtrate was discarded, and the adsorption column was placed in the collection tube. The empty tube was centrifuged at 12,000×g for 2 min.

i) The adsorption column was placed in a new 1.5 ml centrifuge tube. 30-100 μl of Elution Buffer preheated to 70° C. was added to the center of the membrane of the adsorption column, left to stand at room temperature for 3 min, and then centrifuged at 12,000×g for 1 min.

Note: for DNA-rich tissues, 30-100 μl of Elution Buffer was further added to repeat the elution.

j) The adsorption column was discarded. The DNA was stored at 2-8° C., with measured and recorded concentration. It was required to be placed at −20° C. for long-term storage.

4. T7E1 Digestion Experiment (1) Using the genomic DNA extracted from 293T cells transfected with pX601-sgRNA1 to pX601-sgRNA7 plasmids as above, around the target site, the extracted genomic DNA was amplified using the upstream and downstream primers correspondingly designed and synthesized for each of the aforementioned sgRNAs, for PCR of DNA fragments (7 groups in total, named J1-J7, respectively).

(2) The liquid recovery kit (OMEGA Gel Extraction Kit (200) D2500-02) was used to recover the liquid DNA from the above PCR products, and the DNA recovery protocols were as follows:

a) An equal volume of membrane binding solution was added to the PCR reaction product (1 μL of membrane binding solution per 1 mg gel cut and recovered), heated at 50-60° C. for 7 min until all the gels were completely dissolved, mixed by vortexing, and recovered by column;

b) The above liquid was dropped into the recovery column for centrifuging at 10,000×g for 1 min, and the filtrate was discarded;

c) 700 μL of Washing Buffer was added and centrifuged at >13,000×g for 1 min, and the filtrate was discarded;

d) Step c) was repeated;

e) The empty tube was centrifuged at >13,000×g for 10 min;

f) The centrifuge column was transferred to a new 1.5 mL Ep tube and marked. 20-30 μL of Elution Buffer or ddH₂O was added and kept at room temperature for 2 min;

g) After centrifuging at >13,000×g for 1 min, the adsorption column was discarded. The DNA was stored at 2-8° C., with measured and recorded concentration. It was required to be placed at −20° C. for long-term storage.

(3) Validation of sgRNA Efficiency by T7E1 Digestion Experiment

The product obtained by PCR recovery or gel cutting recovery as above was subjected to the T7E1 digestion reaction.

a) Annealing system for T7E1 digestion (19.5 µL):

| Reagent Volume | (µL) |
| --- | --- |
| NEB Buffer 2 | 2 |
| PCR or gel cutting recovery product | X (500 ng or 1,000 ng) |
| Deionized H₂O | ad 19.5 | b) Annealing program for T7E1 digestion:

| 95° C. | 2 min |
| --- | --- |
| 95° C. to 85° C. | Temperature decreased at 2° C./s |
| 85° C. to 25° C. | Temperature decreased at 0.1° C./s |
| 16° C. | ∞. | c) Reaction system for T7E1 digestion

| Reagent Volume | (µL) |
| --- | --- |
| Annealing product | 9.75 or 9.5 |
| T7E1 enzyme | 0.25 or 0.5 |

The system was incubated at 37° C. for 20 min.

d) Gel electrophoresis of digestion product

Gel formulation: 2.5% gel, with double dye added.

Gel electrophoresis program: voltage 140 V, 20 min to 30 min.

e) The gel electrophoresis results were checked.

Figure 2:
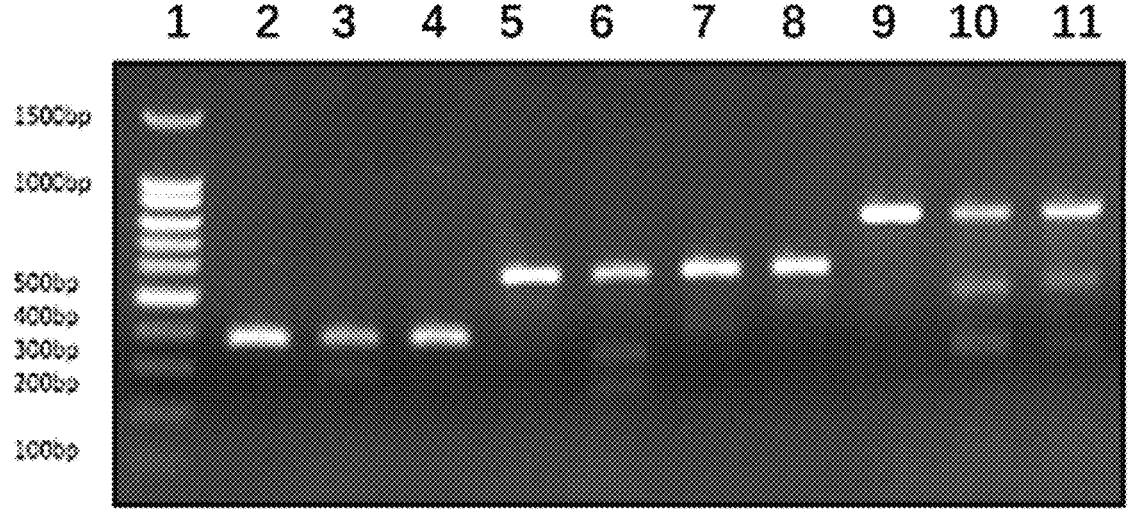
FIG. 2 shows the electrophoretogram of the fragments after cleavage of CYP4V2-HITI-sgRNA1-7 described in the present application, indicating the good cleavage effect of sgRNA1-4.
Figure 3A:
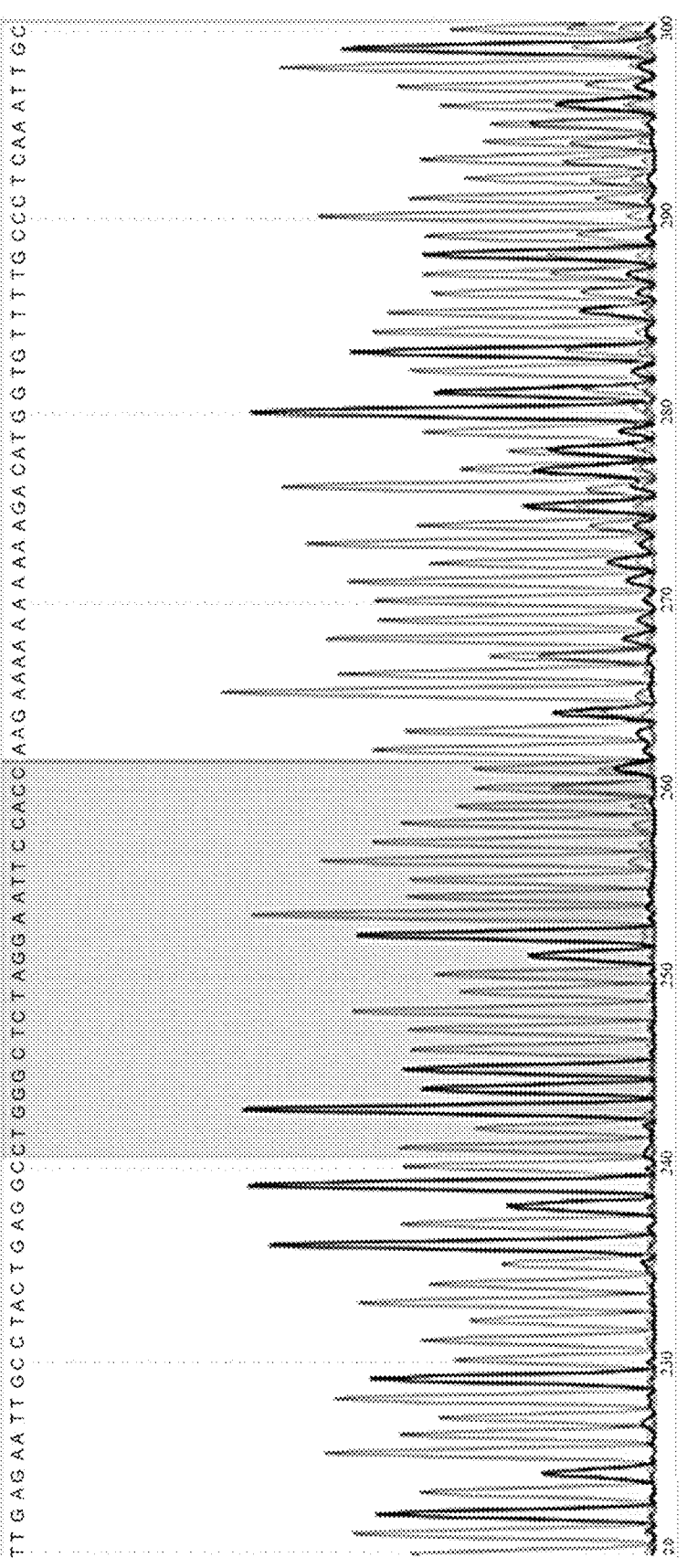
FIGS. 3A-3D show the sequencing results of the fragments containing cleavage sites after cleavage of CYP4V2sgRNA1-4 described in the present application, indicating the good cleavage effect of sgRNA1-4.
Figure 3B:
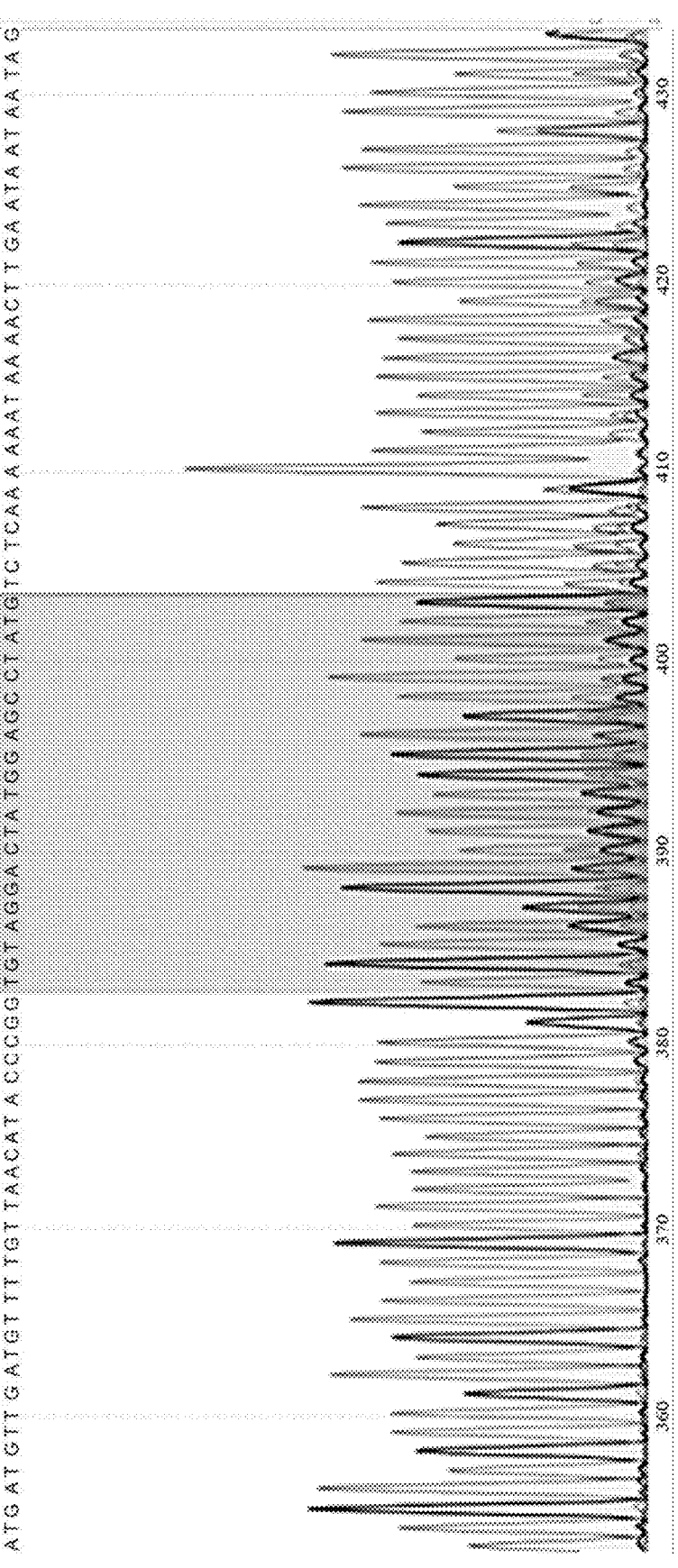
Figure 3C:
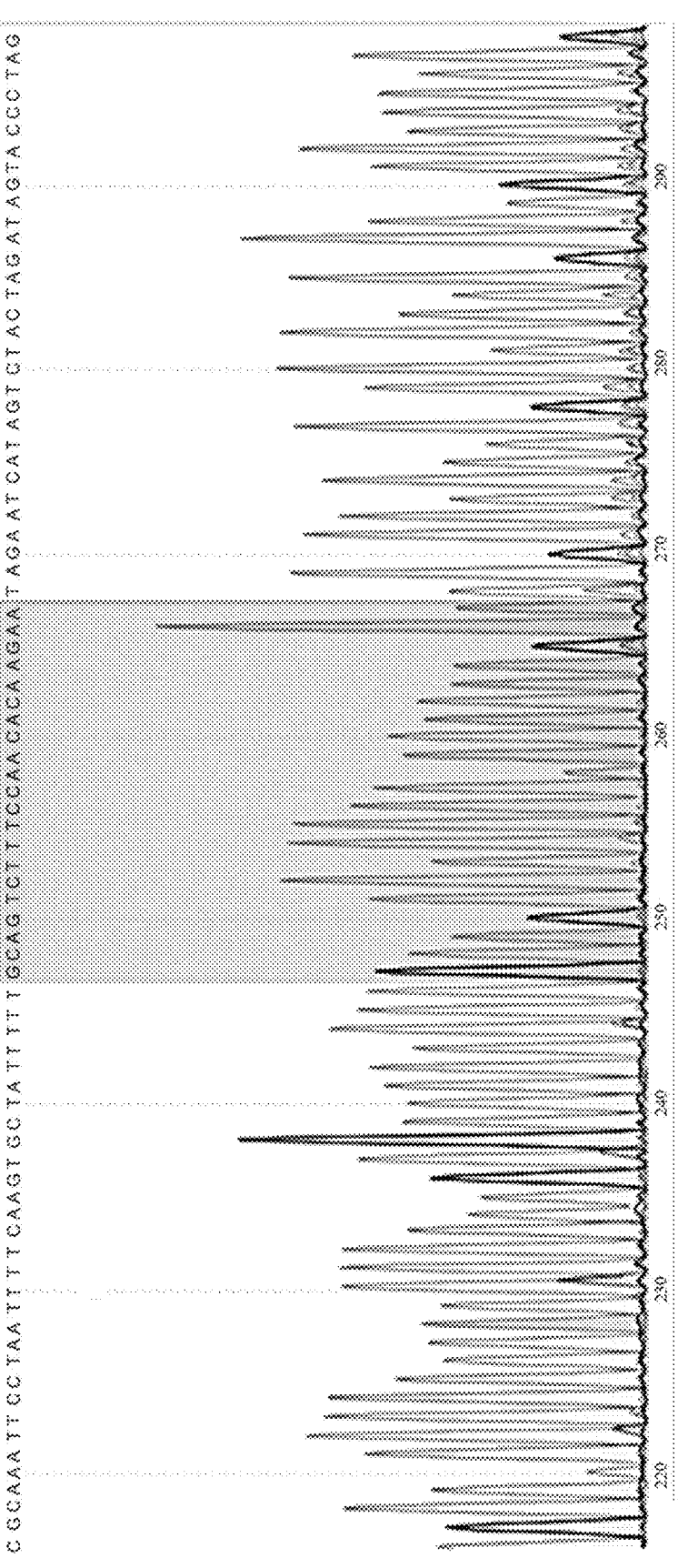
Figure 3D:
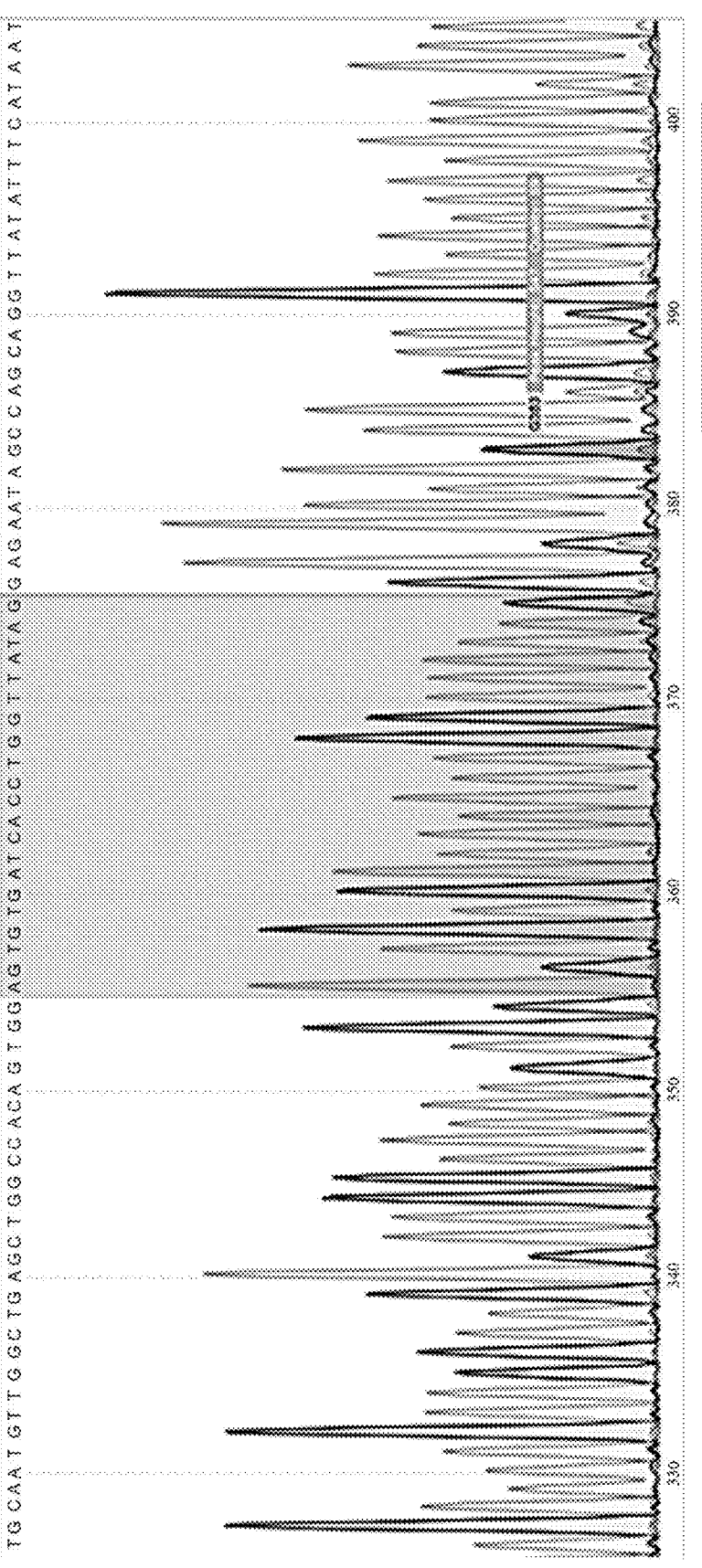

The digestion results were shown in FIG. 2, wherein Lane 1 was the electrophoresis result of the marker, Lane 2 was the electrophoresis result of the negative control (i.e., without sgRNA), Lane 3 was the result of the fragment length after sgRNA1 cleavage, Lane 4 was the result of the fragment length after sgRNA5 cleavage, Lane 5 was the electrophoresis result of the negative control, Lane 6 was the result of the fragment length after sgRNA2 cleavage, Lane 7 was the result of the fragment length after sgRNA6 cleavage, Lane 8 was the result of the fragment length after sgRNA7 cleavage, Lane 9 was the electrophoresis result of the negative control, Lane 10 was the result of the fragment length after sgRNA3 cleavage, and Lane 11 was the result of the fragment length after sgRNA4 cleavage.

The amplification primers, fragment lengths, and fragment lengths after cleavage for each fragment were shown in Table 3.

TABLE 3

Fragment length after sgRNA cleavage by CYP4V2-HITI method

| Template | Primer | Fragment length after amplification | Fragment length after cleavage |
| --- | --- | --- | --- |
| J1 | P1.5-F (SEQ ID NO: 42) and P1.5-R (SEQ ID NO: 43) | 363 bp | 90 bp + 273 bp |
| J2 | P2.6.7-F (SEQ ID NO: 44) and P2.6.7-R (SEQ ID NO: 45) | 542 bp | 237 bp + 305 bp |
| J3 | P3.4-F (SEQ ID NO: 46) and P3.4-R (SEQ ID NO: 47) | 754 bp | 297 bp + 457 bp |
| J4 | P3.4-F and P3.4-R | 754 bp | 289 bp + 465 bp |
| J5 | P1.5-F and P1.5-R | 363 bp | 108 bp + 255 bp |

TABLE 3-continued

Fragment length after sgRNA cleavage by CYP4V2-HITI method

| Template | Primer | Fragment length after amplification | Fragment length after cleavage |
| --- | --- | --- | --- |
| J6 | P2.6.7-F and P2.6.7-R | 542 bp | 177 bp + 365 bp |
| J7 | P2.6.7-F and P2.6.7-R | 542 bp | 98 bp + 444 bp |

5. Gene Sequencing for PCR Fragments Containing Cleavage Sites of Genomic DNA (Nested Peak Test)

The amplified DNA fragments J1-J7 as above were sequenced, and the sequencing maps were shown in FIGS. 3A-3D. It could be found that sgRNAs 1, 2, 3, and 4 have relatively significant cleavage effects.

Example 2. Validation of the Effect of sgRNA Target on Cleavage

I. Designs for pMD19-T Minigene Plasmids Corresponding to the Four sgRNAs as Well as Controls Thereof (Negative and Positive Plasmids)

After insertion in accordance with the donor HITI method, the characteristics of PAM+3 bp sgRNA/18 bp sgRNA fragment would remain. The minigenes 1, 2, 3, and 4 were designed to correspond to sgRNAs 1, 2, 3, and 4. The minigene fragments were shown in FIG. 4.

II. Construction Protocols for Minigene Plasmid

1. Synthesis of minigene DNA fragments as well as positive control (normal wild-type intron, not affecting the cleavage) and negative control (mutated intron of patient, affecting the cleavage) DNA fragments.

2. Digestion of plasmid vector

Figure 5:
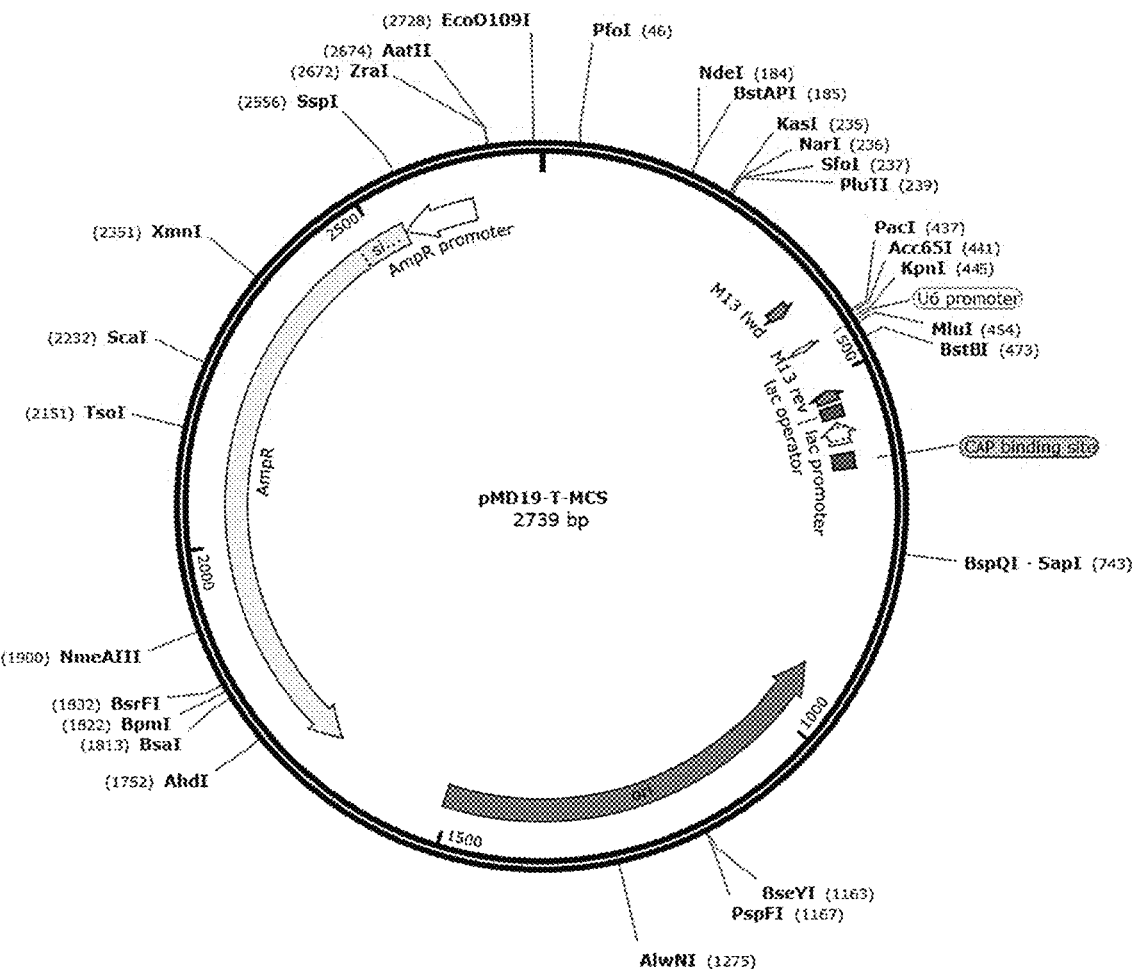
FIG. 5 shows the plasmid map of PMD-19T-MCS described in the present application.

The plasmid vector was PMD-19T-MCS, and its plasmid map was shown in FIG. 5.

(1) The Plasmid was Digested With Both KpnI Enzyme and MluI Enzyme.

In the CutSmart buffer, the KpnI enzyme and MluI enzyme were incubated with the minigene at 37° C. for 30 min. A 2.5% electrophoresis gel was formulated, with double dye added. The digested product was subjected to the electrophoresis under a voltage of 140 V for 20 min to 30 min. After electrophoresis, the gel was cut for purification.

(2) Gel Recovery of the Linearized Vector After Digestion

The liquid recovery kit (OMEGA Gel Extraction Kit (200) D2500-02) was used to recover the liquid DNA from the above PCR products, and the DNA recovery protocols were as follows:

a) An equal volume of membrane binding solution was added to the PCR reaction product (1 µL of membrane binding solution per 1 mg gel cut and recovered), heated at 50-60° C. for 7 min until all the gels were completely dissolved, mixed by vortexing, and recovered by column;

b) The above liquid was transferred into the recovery column for centrifuging at 10,000×g for 1 min, and the filtrate was discarded;

c) 700 µL of Washing Buffer was added and centrifuged at >13,000×g for 1 min, and the filtrate was discarded;

d) Step c) was repeated;

e) The empty tube was centrifuged at >13,000×g for 10 min;

f) The centrifuge column was transferred to a new 1.5 mL EP tube and marked. 20-30 µL of Elution Buffer or ddH₂O was added and kept at room temperature for 2 min;

g) After centrifuging at >13,000×g for 1 min, the adsorption column was discarded. The DNA was stored at 2-8° C., with measured and recorded concentration. It was required to be placed at −20° C. for long-term storage.

(3) Ligation

The recovered vector from the previous step and the synthesized minigene1-6 DNA fragments as well as the corresponding positive control were used to prepare the following ligation system (200 μl PCR tube):

| | |
|---|---|
| Vector recovered from step 2 | 1 μl |
| DNA fragment synthesized in step 1 | 1 μl |
| 2x T4 Ligation Buffer | 5 μl |
| T4 Ligase | 1 μl |
| H₂O | 3 μl |
| Total volume | 11 μl |

The ligation reaction system from the previous step was placed at 37° C. for about 1-2 hours to complete the sgRNA vector construction.

(4) Plasmid Transformation a) TransStbl3 competent cells were placed on ice for thawing;

b) 1 μl of ligation product from step 3 was added to 50 μl of competent cells, and incubated on ice for half an hour, subjected to heat shock at 42° C. for 90 s, and kept on ice for 2 min;

c) 500 μl of antibiotic-free medium was added at 37° C. and shaken at 200 rpm for 1 h. Then the system was centrifuged at 800 rpm/min for 5 min, and the supernatant was discarded for remaining about 100 μl. The LB agar medium containing ampicillin was used to screen positive clones;

d) On the next day, the positive colony was picked (500 μl of medium) and shaken for 3-4 hours, 200 μl of which was sent for sequencing.

(5) Plasmid Extraction

The minigene1-4 confirmed correct by sequencing as well as the positive and negative controls (6 plasmids in total) were shaken overnight (50-200 mL), and incubated on a shaker at 37° C. for 12-16 h to amplify the plasmid, and extracted on the next day (shaking for less than 16 h). The plasmid extraction was conducted in accordance with Omega Endotoxin-free Plasmid Maxiprep Kit.

III. Transfection of 293T Cells With Minigene Plasmid 1. 293T Cell Culture 2. 293T Cell Transfection by Polyethyleneimine (PEI) Method (1) 1.5 mL EP tubes were numbered in the above order. 250 μL of DMEM medium (serum-free) was added to each tube, and 1.5 μg of minigene1-4 plasmids as well as the positive and negative controls were successively added according to the above table. After mixing well by vortexing, 7.5 μL of PEI transfection reagent was added to each tube, mixed well by vortexing, and left to stand at room temperature for 20 min before transfection. Another well in the 6-well plate was set as the blank control.

(2) The system was dropwise added to the culture medium (the culture medium in 6-well plate plus serum-free DMEM=2 ml/well), cultured in an incubator, and half of the medium was refreshed within 12-18 hours. On the next day, the GFP expression was observed under a fluorescence microscope to assess the transfection efficiency, and the transfected plasmid was continued to be cultured if the transfection efficiency was good.

(3) Screening of resistant cells a) Solution formulation: 10 mg/ml (mother solution) puromycin was diluted to 1 μg/ml puromycin for cell screening.

b) Medium changing: two days after transfection, 3 ml of 293T cell medium containing puromycin was added to each well (including the negative control group) to screen for transfected positive cells. Then the survival state of the cells was observed every day. The culture medium was refreshed every 2 days, and a corresponding amount of puromycin was added when changing the medium. At the time that the cells in the negative control well were completely dead while the experimental group and the control group had viable cells (indicating successful transfection), the antibiotic screening was terminated and the culture medium was changed to the normal medium.

3. Extraction of Genomic DNA From 293T Cells (1) After the cells in the 6-well plate reached 80-90% confluence, the cells were passaged to a 6 cm culture dish.

(2) After the cells reached 80-90% confluence, the cells were harvested for extracting the genomic DNA. The whole process lasted for about 7-10 days. The genomic DNA was extracted using the cell extraction kit from Vazyme Biotech.

(3) Validation of the RNA level after transfection in 293T cells

1) RNA Extraction

The RNA was extracted using TIANGEN RNA prep Pure Cultured Cell/Bacteria Total RNA Extraction Kit (DP430), and the experimental protocols were as follows:

a) Cell collection i. Collection of suspension cells (the number of collected cells should not exceed $1 \times 10^7$): the number of cells was estimated, followed by centrifugation at 300×g for 5 min. The cells were collected into a centrifuge tube, and all the medium supernatant was carefully removed.

ii. Collection of monolayer adherent cells (the number of collected cells should not exceed $1 \times 10^7$): the medium was removed, and the cells were washed with PBS. After removing the PBS, the PBS containing 0.10%-0.25% trypsin was added to the cells to treat the cells. When the cells were detached from the container wall, the serum-containing medium was added to inactivate the trypsin. The cell solution was transferred to an RNase-free centrifuge tube, and centrifuged at 300×g for 5 min. The cell pellet was collected, and all the supernatant was carefully removed.

b) Lysis treatment

The bottom of the centrifuge tube was flicked such that the cell pellet was loose. An appropriate amount of lysis solution RL was added according to the number of cells (please check whether β-mercaptoethanol had been added before use), and vortexed.

c) All the solution was transferred to a filtration column CS (the filtration column CS was placed in a collection tube), centrifuged at 12,000 rpm (~13,400×g) for 2 min, to collect the filtrate. 1 volume of 70% ethanol (usually 350 μl or 600 μl) was added to the filtrate, and mixed well (the precipitate may appear at this time). The obtained solution and precipitate were transferred into an adsorption column CR3 (the adsorption column CR3 was placed in the collection tube), and centrifuged at 12,000 rpm (~13,400×g) for 30-60 sec. The waste liquid in the collection tube was discarded, and the adsorption column CR3 was placed back in the collection tube.

d) 350 μl of protein-removed solution RW1 was added to the adsorption column CR3, and centrifuged at 12,000 rpm (~13,400×g) for 30-60 sec. The waste liquid in the collection tube was discarded, and the adsorption column CR3 was placed back in the collection tube.

e) Formulation of DNase I working solution: 10 μl DNase I stock solution was added to a new RNase-free centrifuge tube, followed by 70 μl RDD buffer, and mixed gently.

f) 80 μl of DNase I working solution was added to the center of the adsorption column CR3, and left to stand at room temperature for 15 min.

g) 350 μl of protein-removed solution RW1 was added to the adsorption column CR3, and centrifuged at 12,000 rpm (~13,400×g) for 30-60 sec. The waste liquid in the collection tube was discarded, and the adsorption column CR3 was placed back into the collection tube. 500 μl of rinse solution RW was added to the adsorption column CR3 (please check whether ethanol had been added before use), left to stand at room temperature for 2 min, and centrifuged at 12,000 rpm (~13,400×g) for 30-60 sec. The waste liquid in the collection tube was discarded, and the adsorption column CR3 was put back in the collection tube. This step was repeated.

h) After centrifuging at 12,000 rpm (~13,400×g) for 2 min, the waste liquid was discarded. The adsorption column CR3 was left to stand at room temperature for several minutes to completely dry the residual rinse solution in the adsorption material.

i) The adsorption column CR3 was transferred into a new RNase-free centrifuge tube, and 30-100 μl of RNase-free ddH$_2$O was added and left to stand at room temperature for 2 min, then centrifuged at 12,000 rpm (~13,400×g) for 2 min to obtain RNA solution.

2) Reverse Transcription of cDNA

TRAN Transcript one-step super mix kit for gDNA removal and cDNA synthesis (AT311) was used for the reverse transcription of cDNA, and the experimental protocols were as follows:

a) cDNA synthesis and gDNA removal. The components were added as follows and mixed gently.

| Component | Volume |
| --- | --- |
| RNA extracted in step 1 | 50 ng-5 μg/5-500 ng |
| Anchor oligonucleotide (dT)$_{18}$ primer (0.5 μg/μl) | 1 μl |
| or random primer (0.1 μg/μl) | 1 μl |
| or GSP | 2 pmol |
| 2x TS reaction mix\ | 10 μl |
| TransScript ® RT/RI enzyme mix | 1 μl |
| gDNA remover | 1 μl |
| RNase-free water | variable |
| Total volume | 11 μl | b) The reverse transcription procedure was as follows:

| | |
| --- | --- |
| 42° C. | 30 min |
| 85° C. | 5 sec | c) Sample collection

3) PCR on cDNA

4) Sequencing Validation for PCR Product (5) Validation of the Protein Level After Transfection in 293T Cells 1) Protein Extraction a) 293T cells were obtained and lysed. After the cells were washed with PBS, 100-200 μl RIPA lysis buffer (taking a 6-well plate as example) was added, and the protease inhibitor cocktail, phosphatase inhibitor PMSF, and RNase were added if necessary. Then the cells were scraped into an EP tube. The tube was placed on ice for vortexing every 5 min for three times.

b) The lysed cells were centrifuged at 12,000 rpm for 10 min at 4° C. With 50 μl supernatant as input control, 10 μl 6× loading buffer was added and boiled for 5 min. The boiled sample can be stored at 4° C. for short term or at −20° C. for long term.

2) Validation by Western Blot (Protein Hybridization Experiment)

a) The glass plates were aligned and then put into the shelf, and the clips on both sides were tighten. The short glass was on the outside and the long glass was on the inside. Then they were stuck vertically on the shelf for gel filling. During operation, the glasses on both sides should be aligned to avoid gel leakage. Water was added to check for leakage before gel filling. When formulating the gel, TEMED was added in the last step, then shaken well immediately for gel filling. During gel filling, the tip was along the corner to avoid air bubbles. The distance between the gel surface and the short glass was 1-2 cm. The absolute ethanol was added to press the gel.

b) When there was an obvious dividing line between the absolute ethanol and the gel, it indicated that the gel had solidified. After another 3 minutes for full solidification of the gel, the layer of absolute ethanol above the gel was poured off and dried with paper. The concentrating gel was formulated according to the ratio in the instructions, and the comb was inserted to wait for gel solidification. Please be noted that the comb should be kept horizontal when inserting.

c) Sample loading d) Electrophoresis: the loading amount for each lane in the minigel usually did not exceed 20 μg of total protein. The ionic strength was kept consistent in each sample (including markers and blank lane without samples) to the greatest extent. During electrophoresis, the voltage for running in the concentrating gel was 80 V, and the voltage for running in the separating gel was 120 V. The higher the voltage, the faster the separation. The electrophoresis generally took 1-2 h, and may be terminated when the bromophenol blue was about to run out of the gel.

e) Membrane transfer i. The placement sequence from the gel to the membrane was as follows: black side of the clamp-sponge pad-filter paper-gel-membrane-filter paper-sponge pad-white side of the clamp. Then the entire device was fully immersed in the buffer. Among them, the PVDF membrane needed to be first soaked in methanol, and finally placed in the transfer solution for electrophoresis.

ii. The clamp was placed in a transfer tank with the black side of the clamp facing the black side of the tank and the white side of the clamp facing the red side of the tank.

iii. It is necessary to add ice in the transfer tank for cooling down, and a voltage of 120 V and a constant current of 200 mA were used for membrane transfer. The larger the protein molecule, the greater the voltage/current, and the longer time the transfer time required.

f) Blocking

The membrane was removed and then blocked with TBS solution containing 5% skimmed milk for more than 1 hour.

Please be noted that the side of the membrane that contacts to the gel should face up.

g) Antibody incubation and detection

Primary antibody incubation: the antibody was diluted with TBST containing 2.5% skimmed milk in a ratio of 1:1000, and incubated at room temperature for 1.5-2 h, or overnight at 4° C. Membrane washing: the membrane was washed 3 times with 0.1% TBST, 10 min each time. Secondary antibody incubation: the TBST solution containing 2.5% skimmed milk was diluted in an appropriate ratio, and incubated at room temperature for 2 h. Membrane washing: the membrane was washed 3 times with 0.1% TBST (10 min each time), then washed with TBS for 10 minutes, and bolted up with filter paper on the flank of the membrane. The membrane was placed on a plastic wrap soaked with ECL chromogenic solution mix (1 ml), and the plastic wrap was folded. Finally, it was detected with a gel imaging system.

Figure 6A:
FIGS. 6A-6C show the effects of sgRNA1-4 described in the present application on the cleavage, indicating that sgRNA1-4 does not affect the mRNA cleavage.
Figure 6B:
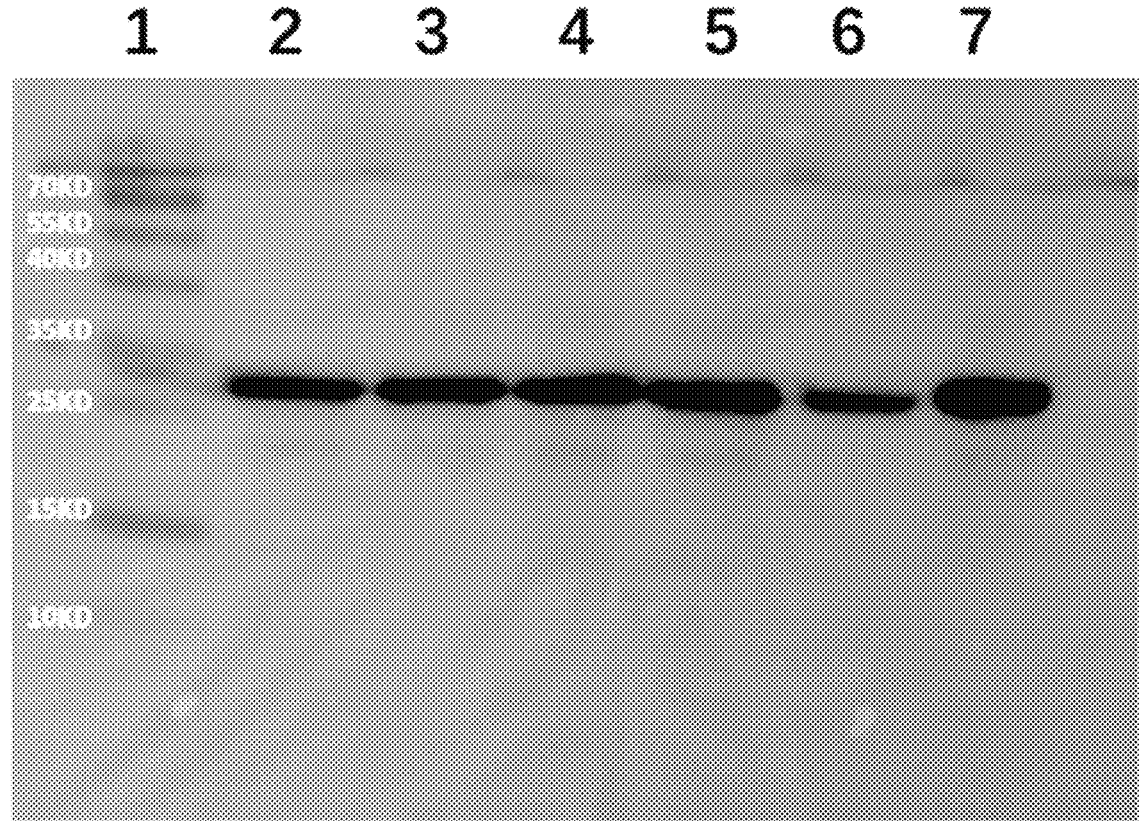
Figure 6C:
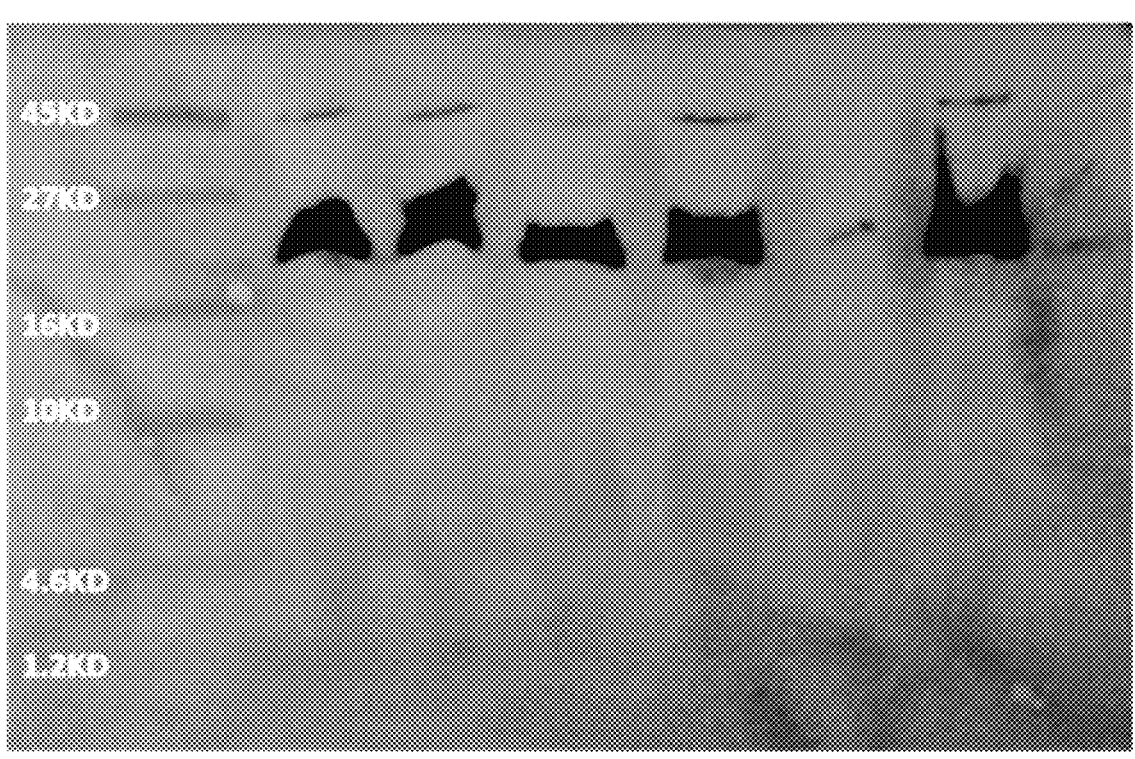

The results of Western Blot were shown in FIGS. 6A-6B. FIG. 6A showed the expression of β-actin in each group of cells. Lane 1 was Marker, Lane 2 was minigene 1, Lane 3 was minigene 2, Lane 4 was minigene 3, Lane 5 was minigene 4, Lane 6 was the negative control, and Lane 7 was the positive control. In each group, β-actin was expressed and the expression level was essentially the same, indicating that the loading amount was the same and the results were comparable. FIG. 6B showed the expression of green fluorescent proteins (GFP) in each group of cells. The groups represented by each lane were consistent with those in FIG. 6A. The results showed that in each group, the expressions of minigenes 1-4 were consistent with the positive control (intron fragment from normal human, which does not affect splicing), in all of which the GFP was expressed; while the negative control (intron fragment from patient, which affected splicing) was weaker in expression. FIG. 6C showed the expression of the tag protein (Flag) in each group of cells. The groups represented by each lane were consistent with those in FIG. 6A. The results showed that Flag was not expressed in the negative control group, but expressed in each experimental group and positive control group. Thus, the results showed that sgRNAs 1-4 had no effect on cleavage.

Example 3. Design and Screening for the Donor

I. Vector Construction:

The sequence between intron 6 and exons 7-11 of wild-type CYP4V2 gene was used as the donor sequence. The donor sequence and the EGFP reporter gene were constructed together into the pX601 vector (pX601-sgRNA1 to pX601-sgRNA4 vectors for sgRNAs 1-4) to obtain the pX601-donor (1-4)-EGFP vector. The pX601-sgRNA (1-4) vector described in Example 1 was used as the sgRNA vector. The pX601 plasmid map was shown in FIG. 1.

Among them, the length of intron 6 was adjusted according to the sgRNA cleavage site, the donor sequence for exons 7-11 were set forth in SEQ ID NO: 39, and the EGFP sequence was set forth in SEQ ID NO: 40.

II. Transfection of iPSCs by PEI Method

1. The detailed protocols were as follows:

Taking the sgRNA1 group as example:

(1) The iPSC cells were seeded in four 6-well plates, and transfected when the cell density reached 80%;

(2) The first group (blank control group): 1.5 μg of pX601 plasmid was added to a 1.5 ml tube;

The second group (experimental group): 1.5 μg of pX601-sgRNA1 plasmid (providing SaCas9) as constructed above and 1.5 μg of pX601-Donor-EGFP plasmid were added to a 1.5 ml tube;

250 μl of serum-free DMEM medium was added respectively to the two tubes and mixed well, followed by 12 μg of PEI (1 mg/ml), mixed well immediately, and incubated at room temperature for 20 min;

(3) The mixed solution was dropwise added to the medium, cultured in the incubator, and half of the medium was refreshed after 24 hours.

The experimental protocols for sgRNA 2-4 groups were the same as those for sgRNA1 group.

III. Screening of Resistant Cells

Solution formulation: 10 mg/ml (mother solution) puromycin was diluted to 1 μg/ml puromycin.

Figure 7:
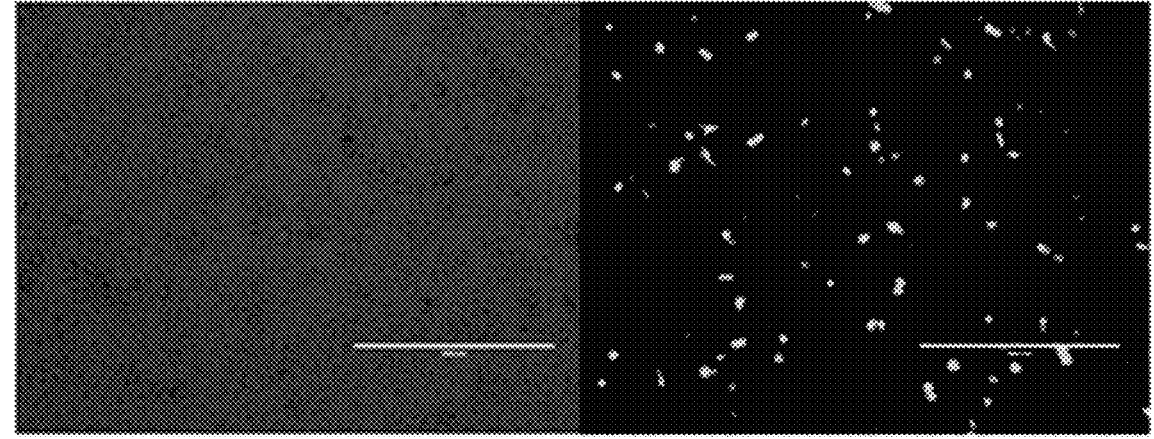
FIG. 7 shows the results of transfected cells in the Donor screening experiment described in the present application, indicating that the vector containing the donor was successfully transfected into the cells.

Medium refreshment: 3 ml of the medium containing 1 μg/ml puromycin was added to each well. The medium was refreshed every day, and the death state of the cells was observed continuously. The transfection effects for each experimental group and blank group were similar. Thus, a representative figure for transfection was selected, and the transfection effect was shown in FIG. 7. The left panel in FIG. 7 was the blank control, and the right panel was the cells after transfection. It could be seen that the fluorescent proteins were expressed in the cells, indicating that the transfection effect was very good.

IV. Extraction of Cell DNA, and Validation of Sequence Repair Results by Sequencing The genomic DNA was extracted using the cell extraction kit from Vazyme Biotech. According to the sequencing results, it could be known that the pX601-sgRNA-Donor1.2.3.4 vectors were effective in repair.

Example 4. In Vitro Validation of sgRNA Gene Editing Efficiency Using 3D Retinal Tissue I. Extraction and Culturation of Renal Epithelial Cells From Patients Using the renal epithelial cell isolation and culture kit provided by Beijing Cellapy, the experimental protocols were as follows:

1. The UrinEasy® isolation complete medium, supplements, gelatin, and washing solution were brought to the cell room.

2. The 12-well plate, 50 ml centrifuge tube, 15 ml centrifuge tube, electric pipettor, pipette, sucker, 5 ml pipettor and tips, and 1 ml pipettor and tips were irradiated under UV lamp; and a water bath kettle at 37° C. was turned on.

3. Urine collection: with gloves and disinfection, the midstream urine was collected, and sealed with sealing film.

4. 750 μL/well of gelatin was added to coat the bottom of the dish (3 wells) for not less than half an hour, and kept at 37° C.

5. The outer surface of the urine bottle was disinfected with 75% alcohol, and the urine was dispensed into a 50 mL conical-bottom centrifuge tube. The tube was sealed and centrifuged at 400×g for 10 min.

6. The UrinEasy® isolation complete medium+supplements were removed and formulated (5 mL of basic medium per 0.5 mL of supplements).

7. Along the upper surface, the supernatant was slowly aspirated by pipette to 1 ml with the minimum speed.

8. The liquid was resuspended in a 15 ml centrifuge tube, 10 ml of washing solution was added and mixed well, then centrifuged at 200×g for 10 min.

9. The gelatin was aspirated from the 12-well plate, and the plate was washed once with the washing solution (500 μL). 750 μL of UrinEasy® isolation complete medium was added to each well and kept at 37° C.

10. The 15 ml centrifuge tube was taken out, and 0.2 mL of cell pellet remained.

11. The cell pellet was resuspended with UrinEasy® isolation complete medium: one well for male and two wells for female, denoted as day 0 (D0).

12. Observation:

D1: whether there was contamination was observed;

D2: the isolation medium was supplemented—female: 500 μl/well; male: 250 μl/well;

D4: If the cells were not adhered: half volume of the medium was changed every two days by slowly adding 1 mL of isolation complete medium along the wall.

13. Until the adherence occurred: after the cells appeared to adhere (3~7 days or 9~10 days), UrinEasy® expansion complete medium was selected for culturing. The cells were cultured for two days, and the full volume (500 μL) of medium was changed. At approximately 9~12 D (not exceeding 14 D) after adherence, the cells at 80-90% confluence were respectively passaged to 6-well plate, 6 cm dish, and 10 cm dish, and then frozen for later use.

II. Induction of iPSCs

The patient-derived (c.802-8_810del17bpinsGC) renal epithelial cells were induced into iPSCs in accordance with the following protocols:

1. The somatic cells were digested and passaged when the cells reached 70-90% confluence. The cells were seeded in a 96-well plate with a controlled density of 5,000 to 15,000 cells/well. 3 density gradients might be set according to the cell conditions, with 3 duplicate wells for each gradient. The day of cell seeding was recorded as day −1.

2. Day 0: The confluence and state of cells were observed under the microscope, and duplicate wells with different gradients were selected for digestion and counting. The wells with 10,000-20,000 cells were chosen for reprogramming. The Reprogramming Medium A was prepared according to the table below:

| Reprogramming Medium A | Volume |
| --- | --- |
| Somatic Cell Culture Medium | 10 mL |
| Reprogramming Supplement I | 10 μL |

3. The Reprogramming Supplement II was first centrifuged, and then 97 μL of Reprogramming Medium A was added to the tube of Reprogramming Supplement II, and mixed well to prepare the Reprogramming Medium B. 100 μL of Reprogramming Medium B was added to a chosen eligible 96-well, and the plate was placed back into the incubator.

4. Days 1-2: The cells were observed under the microscope and photographed to record the changes in cell morphology. If the cell morphology was obviously changed, the Reprogramming Medium B was removed and replaced with the Reprogramming Medium A for further culturing. If the morphological changes were not obvious, the medium might not be changed.

5. Day 3: If the cell morphology had subjected to obvious deformation in the first two days, and the cell growth rate was relatively fast, the cells were digested by trypsin and passaged. Depending upon the cell state and amount, the cells were transferred to 2-6 wells of a 6-well plate, and the Reprogramming Medium C was added to form the single-cell adherence as much as possible. The reprogramming medium C was prepared according to the table below:

| Reprogramming Medium C | Volume |
| --- | --- |
| Reprogramming Medium A | 9.8 mL |
| Reprogramming Supplement III | 5 Ml |

6. Day 4: The adherence of the cells was observed. If most of the cells adhered well, the medium was replaced with fresh Reproeasy® somatic cell culture medium (Cellapy, CA5001050) for further culturing.

7. Day 5: The cells were observed under the microscope. If a small clone cluster (clone pellet with more than 4 cells) was formed, the somatic cell culture medium was replaced with Reproeasy® Human Somatic Cell Reprogramming Medium. If no small clone cluster was formed, the cells were further observed for one or two days before replacing the medium with Reproeasy® Human Somatic Cell Reprogramming Medium.

8. Days 6-8: The cells were observed under the microscope. If the small clone cluster became larger and there were more than 10 cells in a clone pellet, Reproeasy® Human Somatic Cell Reprogramming Medium was directly replaced with PSCeasy® Human Pluripotent Stem Cell Medium (or PGM1 Human Pluripotent Stem Cell Medium). If a relatively large number of dead cells were observed before changing the medium, the cells might be washed with PBS equilibrated at room temperature before changing the medium.

9. Days 9-20: The cells were observed under the microscope and photographed to record the changes in cell morphology. The fresh PSCeasy® Human Pluripotent Stem Cell Medium equilibrated at room temperature was replaced daily.

10. Day 21: The cells were observed under the microscope. If a single cell clone could fill the entire 10× field of view, a 1 mL syringe needle (or other equipment such as glass needles) was used to cut and pick the clone into a 48-cell plate coated with Matrigel in advance (if the clone was in good condition with massive cells and fast growth, it could be directly picked into a 24-well plate).

11. The clone was picked out and seeded with PSCeasy® Human Pluripotent Stem Cell Resuscitation Medium. After the cells adhered to the wall, the medium was replaced with PSCeasy® Human Pluripotent Stem Cell Medium for further culturing to the desired passage.

III. Induction of Patient's 3D Retina

The detailed protocols were as follows:

| Stage 1 | D0 | The iPSCs were seeded in a T25 flask at a density of 30,000/cm² and cultured until the cell density reached about 70%. | E8 medium |
| Stage 2 | D1 | The cells were digested with Dispase (2 mg/ml), and 3:1 E8:NIM + rock inhibitor (Y27632) medium was added to suspend the | E8 + NIM |

-continued

| | | | | |
|---|---|---|---|---|
| | | cultured cells in a 10 cm dish. (The embryoid body (EB) was formed on the next day and existed alone.) | | |
| | D2 | The medium was changed (E8:NIM = 1:1). | | |
| | D3 | The medium was changed (E8:NIM = 1:3). | | |
| | D4-5 | The medium was changed (Complete NIM). | | |
| | D6 | The medium was changed (NIM + 50 ng/ml (bone morphogenetic protein 4)). | BMP4 | |
| | D7 | EBs with good morphology (single-chamber, clear) were chosen, and 1 ml (about 200 EBs) medium was dropwise added to the adherent 6-well plate, and then (1 ml NIM + 250 µl FBS)/well was added. | NIM | |
| | D8 | The medium was changed ((4 ml NIM + 25 ng/ml BMP4)/well). | | |
| | D9-15 | Half of the medium was refreshed every other day (NIM medium). | | |
| | D16 | The aggregated cell pellets were transferred into a 15 ml centrifuge tube with a 10 µl pipette tip, such that they sunk to the bottom naturally. The supernatant was removed, and 5 ml RDM was added to resuspend. The suspension was seeded into a 6 cm dish, and the medium was refreshed every 2-3 days. It was followed by mechanical separation and suspension culture in RDM. | | |
| Stage 3 | D18-20 | By observation under 4x microscope, the retinal neurospheres (pellets) with bright outer rings on the surface were collected gently and slowly, and transferred to a 15 ml centrifuge tube containing 5 ml RDM. The collected retinal neurospheres (pellets) were transferred into a 6 cm dish. | RDM | |
| | D20-30 | The medium was changed every 2-3 days. The retinal organoids were continually chosen based on the presence or absence of bright outer ring in the appearance. During this period, some organoids might be gradually transformed towards non-retinal neurospheres. After 30 days, the remaining retinal neurospheres could maintain their morphology ever since. | | |

IV. Construction and Coating of AAV8 Virus

1. Plasmid amplification: the constructed AAV vector, packaging plasmid, and helper plasmid should be subjected to the endotoxin-free maxiprep extraction. The Qiagen maxiprep extraction kit was used for the maxiprep plasmid extraction in accordance with the same protocols as above.

2. AAV8-293T cell transfection: the cell density was observed on the day of transfection, and at 80-90% confluence, the vector plasmid, packaging plasmid, and helper plasmid were used for transfection.

3. AAV8 virus collection: the virus particles were present in both packaging cells and culture supernatant. Both the cells and the culture supernatant could be collected for a good yield.

4. After AAV purification, it was stored at –80° C. for long-term storage.

V. In Vitro Validation of sgRNA Gene Editing Efficiency Using 3D Retinal Tissue

1. Use of AAV8 in infecting 3D retinal tissue: the state of the tissue was observed. When the 3D retinal tissue grew well, the AAV8 virus carrying the target plasmid may be used for transfection.

2. The gene editing efficiency was verified.

(1) T7E1 Digestion Experiment

The protocols were as shown in T7E1 digestion experiment in Example 1.

(2) TOPO PCR Cloning

In order to quantify the editing efficiencies of pX601-CYP4V2-sgRNA and PMD19-T-donor as well as statistically analyze the cleavage efficiencies of the experimental and control groups, Zero Blunt® TOPOR PCR cloning kit from Invitrogen was used for experiments. The clones were picked and sent for Sanger sequencing.

a) The DNA obtained after infecting the 3D retinal tissue with AAV virus was used as the amplification template, and the DNA polymerase from Platinum SuperFi™ series of Invitrogen was used for PCR reactions. The reaction system was as follows (50 µL system):

| | |
|---|---|
| 5x SuperFi ™ Buffer | 10 µL |
| 10 mM dNTP mix | 1 µL |
| Forward prime | 1.25 µL |
| Reverse primer | 1.25 µL |
| gDNA | 50 ng |
| Platinum ™ SuperFi ™ DNA polymerase | 0.5 µL |
| Diethyl pyrocarbonate (DEPC) H$_2$O | To a total volumn of 50 µL | b) Touch down PCR program:

The detailed protocols were identical to the PCR protocols for sgRNA annealing in Step 3 in Example 1.

c) TOPO PCR cloning reaction was as follows:

| Reagent | Volume (µL) |
|---|---|
| Fresh PCR product | 0.5-4 |
| Salt solution | 1 |
| ddH$_2$O | ad 5 |
| pCR ™-Blunt II-TOPO ® | 1 |
| Total volumn | 6 |

The above system was prepared, mixed gently, and left to stand at room temperature for 5 min;

Then the system was placed on ice for the transformation in competent cells.

d) TOPO PCR cloning reaction for the transformation in competent cells

2 µL of the above TOPO PCR cloning reaction liquid was added to 50 or 100 µL of competent cells, and placed on ice for 5-30 min. The system was subjected to heat shock at 42° C. for 30 sec without shaking. It was immediately transferred on ice, and 250 µL of S.O.C. medium was added. The system was shaken at 200 rpm at 37° C. for 1 h for thawing. A corresponding amount of LB medium (25 µg/mL bleomycin added) and 100 µL of the above bacteria solution were used for plating, and cultured in an incubator at 37° C. overnight.

e) The clones were picked and sent for Sanger sequencing.

The next morning, the bacteria plates were taken out, and 80 clones per plate were picked, shaken at 200 rpm at 37° C. for 3-4 h. 200 µL for each clone sample was sent for Sanger sequencing.

f) The Sanger sequencing results were analyzed and subjected to statistical analysis.

Example 5. Validation of Gene Editing Efficiency in a Humanized Mouse Model

I. Construction of Humanized Mice

The construction of humanized mice was completed by Beijing Biocytogen Co., Ltd.

1. Preparation of Humanized Mice

For the human mutation site, the Beijing Biocytogen Gene Biotechnology Co., Ltd. was commissioned to construct the humanized mouse models for CYP4V2.

2. Technical Contents:
  (1) Design and construction of the sgRNA that recognizes the target sequence;
  (2) Construction of the CRISPR/Cas9 vector for the cleavage of target gene;
  (3) Activity detection of sgRNA/Cas9;
  (4) Design and construction of the targeting vector for gene knock-in with the replacement of exons 6-8 (including intron sequence) in accordance with the design scheme;
  (5) In vitro transcription of sgRNA/Cas9 mRNA;
  (6) Injection of sgRNA/Cas9 mRNA and targeting vector into mouse fertilized eggs;
  (7) Detection and propagation of F0 generation mice with CYP4V2 gene knock-in;
  (8) Acquisition and genotype identification of F1 generation heterozygous mice with CYP4V2 gene knock-in (southern blotting DNA hybridization validation, including one exogenous probe and one endogenous probe).
3. Technical Method:
  (1) Amplification and sequencing of the target sequence in mouse genome, design and construction of CRISPR/Cas9 vector plasmid for the target sequence, and activity detection:
  (2) Extraction of mouse genomic DNA and amplification of the sgRNA recognizing the target sequence;
  (3) Design and construction of the CRISPR/Cas9 vector plasmid for the cleavage of target sequence;
  (4) Activity detection of sgRNA/Cas9 using the detection kit independently developed by Biocytogen;
  (5) Design and construction of the targeting vector for CYP4V2 gene knock-in by selecting highly active sgRNA/Cas9 target site sequence information;
  (6) Pronucleus injection of sgRNA/Cas9 mRNA and targeting vector into mouse fertilized eggs, and acquisition of F0/F1 generation positive mice. This experimental process mainly included the following:
  In vitro transcription of sgRNA/Cas9 mRNA;
  Collection of mouse fertilized eggs;
  Injection of mouse fertilized eggs and targeting vector into the mouse fertilized eggs;
  Transplantation of the fertilized eggs into the fallopian tubes of surrogate mice;
  Genotype identification and propagation of F0 generation mice with humanized point mutation of CYP4V2 gene;
  Acquisition and genotype identification of F1 generation mice with humanized point mutation of CYP4V2 gene (including PCR detection and Southern blotting hybridization validation).
II. Feeding and Breeding
  After obtaining the two kinds of humanized mice, the F1 generation heterozygous mice were inbred to obtain a sufficient number of F2 or F3 generation humanized homozygous mice as soon as possible for AAV virus injection.
III. Injection of AAV Virus Into the Subretinal Space in Mice
  The pX601-sgRNA (providing SaCas9) and pX601-Donor-EGFP vector were packaged into adeno-associated virus and injected into the retina of CYP4V2 mutant model mice to verify the editing and repair efficiency of the designed sgRNA and donor in vivo. Taking pX601-sgRNA1+pX601-Donor1-EGFP as example, the detailed protocols were as follows (the experimental protocols for sgRNA2-4 group were the same).

1. Experimental Design
  (1) Blank control group: physiological saline.
  (2) Experimental group: pX601-sgRNA1 (providing SaCas9) and pX601-Donor-EGFP.
2. Selection of Adeno-Associated Virus (AAV) Serotype
  The AAV2/8 serotype with a better preference for the retina was selected.
3. Virus Packaging
  The pX601-Donor1-EGFP and pX601-sgRNA1 vectors were packaged with AAV2/8 and
  AAV-helper into adeno-associated virus (AAV).
4. Injection Experiment in Mice
  20 CYP4V2 mutant model mice were used in the experiment and divided into 4 groups (5 in each group).
  The experimental protocols were as follows:
  (1) Blank control group: the mice were injected with 2 μl of physiological saline in each eye.
  (2) Experimental group: the packaged pX601-sgRNA1 and pX601-Donor1-EGFP viruses were mixed in equal amounts at a ratio of 1:1, and the mice were injected with 2 μl (1E10vg) in each eye.
  (3) The therapeutic effect was detected after one month. The experimental protocols were as follows:
  (4) The pupils were dilated with 1% atropine at 30 min before injection, and dilated again before anesthetization.
  (5) The mice were anesthetized by intraperitoneal injection at a ratio of 80 mg/kg ketamine and 8 mg/kg xylazine. Then the mice were placed in front of the animal experiment platform of the ophthalmic surgery microscope, and a drop of 0.5% proparacaine was dropped on the eyes of mice for local anesthesia. The fluorescein sodium stock solution was added to the AAV virus at a concentration of 100:1, and mixed by low-speed centrifugation.
  (6) A minipore was pricked by insulin needle in advance in the ciliary pars plana of the mouse eyeball, through which a microsyringe needle passed to enter the vitreous chamber of the mouse eyeball. At this time, an appropriate amount of 2% hydroxymethyl cellulose was dropped on the mouse eyeball such that the mouse fundus could be seen under the microscope. Then the needle was inserted into the contralateral periphery subretinal space while keeping off the lens. The AAV virus with fluorescein sodium was slowly pushed-in, with an injection volume of 1 μl in each eye. The fluorescein sodium served as the indicator for judging whether it was injected into the subretinal space.
  (7) Whether the mouse was normal or not was observed after injection, and the neomycin eye ointment was applied to prevent infection.
IV. Evaluation of the Effect of Gene Editing Therapy:
  The experimental results found that the therapeutic effects of each experimental group were essentially the same, so the pX601-sgRNA+pX601-Donor-EGFP virus group was selected as a representative to illustrate the therapeutic effect of gene editing.
  The effect of gene editing therapy was mainly explained in the following ways:
  The functional changes of mice after treatment were evaluated by ERG (retinal electrophysiology). After treatment, the retinal function of the mutant mouse model was improved;
  After the sections were taken, the morphological changes of the mouse retina were observed by HE staining, and the morphology was close to the condition of the retina of wild-type mouse;

Whether the gene editing therapeutic vector was expressed in the corresponding site of the retina was observed by immunofluorescence staining, and the gene editing therapeutic vector was expressed in the corresponding site of the retina;

The changes of retinal tissue morphology were observed through a series of staining labels for special retinal markers, and it was found that the retinal tissue morphology of mice was improved after treatment.

V. Editing Efficiency Assessment of AAV8-pX601-CYP4V2-SgRNA in Humanized Mice

The validation protocols referred to the section "In vitro validation of sgRNA gene editing efficiency using 3D retinal tissue" in step 5 of Example 4. T7E1 digestion experiment and TOPO PCR cloning experiment were used to verify the gene editing efficiency of sgRNA. It was found that sgRNA could achieve a good gene editing efficiency.

Finally, it should be noted that: the above examples are only used to illustrate the technical solutions of the present application, and are not limitative; although the present application has been described in detail with reference to the above examples, those of ordinary skill in the art should understand that the technical solutions described in the above examples can be modified, or some technical features can be replaced equivalently; and these modifications or replacements do not make the essence of the corresponding technical solutions deviate from the spirit and scope of the technical solutions of the examples of the present application.

What is claimed is:

1. A gRNA targeting polypeptide 2, subfamily V, family 4, cytochrome P450 (CYP4V2) gene, wherein the gRNA comprises the nucleotide sequence set forth in any of SEQ ID NOs: 48, 49, and 51.

2. The gRNA according to claim 1, which binds to a nucleotide sequence comprising the nucleotide sequence set forth in SEQ ID NO: 41.

3. The gRNA according to claim 1, comprising 5'-(X)n-SEQ ID NO: 48, 49, or 51 skeleton sequence-3', wherein X is a base selected from any of A, U, C, and G, and n is any integer from 0 to 15.

4. The gRNA according to claim 1, wherein the gRNA is a single-stranded guide RNA (sgRNA).

5. One or more isolated nucleic acid molecule(s) encoding the gRNA targeting CYP4V2 gene according to claim 1.

6. A method for treating Bietti crystalline dystrophy, comprising the following step: introducing the gRNA of claim 1 into a subject in need thereof.

7. The method according to claim 6, wherein the introducing results in a CYP4V2 protein with a normal function.

8. The method according to claim 6, wherein the introducing comprises injection.

9. The method according to claim 6, wherein the introducing comprises injection in the subretinal space.

10. A vector comprising the one or more isolated nucleic acid molecule(s) according to claim 5.

11. The vector according to claim 10, wherein the vector further comprises a donor nucleic acid molecule comprising a nucleotide sequence as set forth in SEQ ID NO: 39.

12. The vector according to claim 10, wherein the vector is a viral vector.

13. An isolated cell comprising the one or more isolated nucleic acid molecule(s) according to claim 5.

14. The isolated cell according to claim 13, wherein the isolated cell comprises HEK293 cells, kidney epithelial cells, and/or induced pluripotent stem cells.

15. The isolated cell according to claim 13, wherein the isolated cell has been modified to have a cellular differentiation potential.

16. The isolated cell according to claim 13, wherein the cellular differentiation potential comprises the potential to differentiate into a 3D-retinal organoid.

17. A pharmaceutical composition comprising the one or more isolated nucleic acid molecule(s) according to claim 5, and a pharmaceutically acceptable carrier.

18. A kit comprising the one or more isolated nucleic acid molecule(s) according to claim 5.

* * * * *